(12) United States Patent
Burwell

(10) Patent No.: US 12,343,157 B2
(45) Date of Patent: Jul. 1, 2025

(54) ASSESSING MOTIVATED ATTENTION WITH CUE REACTIVITY

(71) Applicant: Neurotype Inc., Minneapolis, MN (US)

(72) Inventor: Scott Burwell, Minneapolis, MN (US)

(73) Assignee: Neurotype Inc.

(*) Notice: Subject to any disclaimer, the term of this patent is extended or adjusted under 35 U.S.C. 154(b) by 643 days.

(21) Appl. No.: 17/229,861

(22) Filed: Apr. 13, 2021

(65) Prior Publication Data

US 2021/0315508 A1    Oct. 14, 2021

Related U.S. Application Data

(60) Provisional application No. 63/010,040, filed on Apr. 14, 2020, provisional application No. 63/010,042, filed on Apr. 14, 2020.

(51) Int. Cl.
*A61B 5/378* (2021.01)
*A61B 5/31* (2021.01)
(Continued)

(52) U.S. Cl.
CPC ............ *A61B 5/378* (2021.01); *A61B 5/31* (2021.01); *A61B 5/372* (2021.01); *A61B 5/384* (2021.01);
(Continued)

(58) Field of Classification Search
None
See application file for complete search history.

(56) References Cited

U.S. PATENT DOCUMENTS

| 5,730,146 A | 3/1998 | Itel et al. | |
|---|---|---|---|
| 6,186,145 B1* | 2/2001 | Brown | A63F 13/52 |
| | | | 600/300 |

(Continued)

FOREIGN PATENT DOCUMENTS

| EP | 2695124 A1 | 2/2014 |
|---|---|---|
| EP | 2906114 A1 | 8/2015 |

(Continued)

OTHER PUBLICATIONS

Littel, M., Euser, A. S., Munafò, M. R., Franken, I. H. A. (2012). Electrophysiological indices of biased cognitive processing of substance-related cues: A meta-analysis. Neuroscience Biobehavioral Reviews, 36(8), 1803-1816. doi.org/10.1016/j.neubiorev.2012.05.001 (Year: 2012).*

(Continued)

*Primary Examiner* — May A Abouelela
*Assistant Examiner* — Samuel C Kim
(74) *Attorney, Agent, or Firm* — Headland Law & Strategy; Matthew J. Smyth

(57) ABSTRACT

A system may include a portable EEG headset configured to capture user EEG signals, a computing device having a graphical user interface, and one or more processors. The one or more processors may be configured to execute instructions to (a) display a sequence of images on the graphical user interface; (b) receive, from the portable EEG headset, user EEG signals that are time-synchronized with the display of the sequence of images; (c) extract from the user EEG signals, one or more event-related potential (ERP) peaks associated with each image; (d) quantify one or more affect-related measures associated with the one or more ERP peaks; and (e) compare the quantified one or more affect-related measures to baseline data to determine a risk to the user.

16 Claims, 12 Drawing Sheets

(51) Int. Cl.
  *A61B 5/372* (2021.01)
  *A61B 5/384* (2021.01)
  *A61B 5/00* (2006.01)

(52) U.S. Cl.
  CPC ..... *A61B 5/0006* (2013.01); *A61B 2560/0431* (2013.01)

(56) References Cited

U.S. PATENT DOCUMENTS

| | | | |
|---|---|---|---|
| 6,572,562 | B2 | 6/2003 | Marshall |
| 6,983,184 | B2 | 1/2006 | Price |
| 8,239,000 | B1 | 8/2012 | Morris et al. |
| 8,386,312 | B2 | 2/2013 | Pradeep et al. |
| 8,392,250 | B2 | 3/2013 | Predeep et al. |
| 8,392,255 | B2 | 3/2013 | Pradeep et al. |
| 8,762,202 | B2 | 6/2014 | Pradeep et al. |
| 8,805,489 | B1 | 8/2014 | Ofek |
| 9,113,801 | B2 | 8/2015 | Dilorenzo |
| 9,336,535 | B2 | 5/2016 | Pradeep et al. |
| 9,339,227 | B2 | 5/2016 | D'Arcy et al. |
| 9,558,425 | B2 | 1/2017 | Wang et al. |
| 9,603,564 | B2 | 3/2017 | Forbes |
| 9,886,981 | B2 | 2/2018 | Pradeep et al. |
| 10,108,264 | B2 | 10/2018 | Le et al. |
| 11,311,228 | B1* | 4/2022 | Oakley ................. A61B 5/0006 |
| 2003/0158497 | A1* | 8/2003 | Graham ................. A61B 5/378 600/558 |
| 2005/0273017 | A1 | 12/2005 | Gordon |
| 2007/0060831 | A1 | 3/2007 | Le et al. |
| 2008/0065468 | A1 | 3/2008 | Berg et al. |
| 2009/0062629 | A1 | 3/2009 | Pradeep et al. |
| 2010/0156617 | A1* | 6/2010 | Nakada ..................... A61B 5/18 340/439 |
| 2011/0118618 | A1* | 5/2011 | John ....................... A61B 5/411 600/544 |
| 2012/0130800 | A1 | 5/2012 | Pradeep et al. |
| 2012/0259240 | A1 | 10/2012 | Llewellyn et al. |
| 2012/0330178 | A1* | 12/2012 | Kraft ....................... A61B 5/378 600/544 |
| 2013/0073396 | A1 | 3/2013 | Pradeep et al. |
| 2013/0131535 | A1 | 5/2013 | Sun et al. |
| 2013/0144184 | A1* | 6/2013 | Regini .................... A61B 5/378 600/558 |
| 2014/0163408 | A1* | 6/2014 | Kocher ................ A61B 5/7275 600/544 |
| 2015/0248470 | A1 | 9/2015 | Coleman et al. |
| 2015/0257673 | A1* | 9/2015 | Lawrence ............ A61B 5/6803 600/383 |
| 2015/0297109 | A1 | 10/2015 | Garten et al. |
| 2017/0347907 | A1 | 12/2017 | Le et al. |
| 2019/0059770 | A1* | 2/2019 | Gunasekar ............. G16H 30/20 |
| 2019/0247654 | A1 | 8/2019 | Alyagon et al. |

FOREIGN PATENT DOCUMENTS

| | | |
|---|---|---|
| EP | 3030151 A1 | 6/2016 |
| EP | 3143933 B1 | 8/2018 |
| WO | WO2008030542 A3 | 3/2008 |
| WO | WO2013177592 A3 | 11/2013 |
| WO | WO2014170897 A1 | 10/2014 |
| WO | WO2015017563 A1 | 2/2015 |
| WO | WO2016143759 A1 | 9/2016 |

OTHER PUBLICATIONS

Luijten, M., Kleinjan, M., & Franken, I. H. (2016). Event-related potentials reflecting smoking cue reactivity and cognitive control as predictors of smoking relapse and resumption. Psychopharmacology, 233(15-16), 2857-2868. https://doi.org/10.1007/s00213-016-4332-8 (Year: 2016).*

Habelt, B., Arvaneh, M., Bernhardt, N., & Minev, I. (2020b). Biomarkers and neuromodulation techniques in substance use disorders. Bioelectronic Medicine, 6(1). doi.org/10.1186/s42234-020-0040-0 (Year: 2020).*

AAN, "Coding FAQs," retrieved from https://www.aan.com/practice/billing-and-coding/coding-faqs/, 5 pages.

Allenby et al., "Neural cue reactivity during acute abstinence predicts short-term smoking relaps," Addict. Biol. 2019, 1-9, 9 pages.

American Academy of Neurology, " Long-term EEG Monitoring FAQs," retrieved from https://www.aan.com/siteassets/home-page/tools-and-resources/practicing-neurologist—administrators/billing-and-coding/coding-faqs/eeg-faq-on-aan-template-1.31.2020-final.pdf, 13 pages.

Anker et al., "Casal Network Modeling of the Determinants of Drinking Behavior in Comorbid Alcohol Use and Anxiety Disorder," Alcohol. Clin. Exp. Res. 2019, 43(1): 91-97, 7 pages.

Anker et al., A network approach to modeling comorbid internalizing and alcohol use disorders, J. Abnorm. Pscyhol. 2017; 126(3): 325-339, 15 pages.

Bach et al., "Incubation of neural alcohol cue reactivity after withdrawal and its blockade by naltrexone," Addict. Biol. 2019, 1-11, 11 pages.

Berridge et al., "Liking, wanting, and the incentive-sensitization theory of addiction," Am. Psychol. 2016, 71(8): 670-679, 17 pages.

Bigdely-Shamlo et al., "Automated EEG mega-analysis II: Cognitive aspects of event related features," NeuroImage 2019, retrieved from https://doi.org/10.1016/j.neuroimage.2019.116054, 40 pages.

Biosemi, "Start your analysis with clean signals from BioSemi systems," retrieved from https://www.biosemi.com/, last visited Mar. 8, 2021, 1 page.

Bouchery et al.,"Type of health insurance and the substance abuse treatment gap," J. Subst. Abuse Treat 2012, 42: 289-300, 12 pages.

Brain Products, "Products by Application," retrieved from https://www.brainproducts.com/products_by_apps.php?aid=5, last visited Mar. 8, 2021, 1 page.

Briggs et al., "Affective picture processing and motivational relevance: Arousal and valence effects on ERPs in an oddball task," International J of Psychophysiology 2009, 17: 299-306, 8 pages.

Brooke, "SUS—A quick and dirty usability scale," retrieved from www.TBISTAffTraining.info, 8 pages.

Burwell et al., "Does Electroencephalogram Phase Variability Account for Reduced P3 Brain Potential in Externalized Disorders?" Clin Neurophysiol. 2014, 125(10): 2007-2015, 24 pages.

Burwell et al., "Reduced premovement positivity during the stimulus-response interval precedes errors: Using single-trial and regression ERPs to understand performance deficits in ADHD," Psychophysiology 2019, 00(e13392): 1-26, 26 pages.

Burwell, "Setting value-based payment goals-HHS efforts to improve US health care," N. Engl. J. Med. 2015, 372 (10): 897-899, 3 pages.

Carpenter et al., "Bootstrap confidence intervals: when, which, what? A practical guide for medical statisticians," Statist. Med. 2000, 19: 1141-1164, 24 pages.

Carretie et al., "EmoMadrid: An emotional pictures database for affect research," Motivation and Emotion 2019, 43: 929-939, 11 pages.

Cinciripini et al., "Benefits of varenicline vs. bupropion for smoking cessation: a Bayesian analysis of the interaction of reward sensitivity and treatment," Psychopharmacology 2017; 234, 1769-1779.

Cofresi et al., "Evidence for incentive salience sensitization as a pathway to alcohol use disorder," Neuroscience and Behavioral Reviews 2019, 107: 897-926.

Colaizzi et al., "Mapping sign-tracking and goal-tracking onto human behaviors," Neuroscience and Biobehavioral Reviews 2020, 111: 84-94.

Compumedics, NeuroScan, retrieved from https://compumedicsneuroscan.com/, last visited Mar. 8, 2021, 4 pages.

Courtney et al., "Neural substrates of cue reactivity: association with treatment outcomes and relapse," Addict. Biol. 2016; 21(1): 3-22, 29 pages.

Debener et al., "How about taking a low-cost, small, and wireless EEG for a walk?" Psychophysiology 2012, 49: 1449-1453, 5 pages.

(56) References Cited

OTHER PUBLICATIONS

Del Zotto et al., "Electrophysiological evidence of perceived sexual attractiveness for human female bodies varying In waist-to-hip ration," Cogn. Affect Behav Neurosci 2017, 17: 577-591, 15 pages.
Deweese et al., "Cigarette cues capture attention of smokers and never-smokers, but for different reasons," Drug Alchol. Depend. 2018; 185: 50-57, 8 pages.
Di Flumeri et al., "The Dry Revolution: Evaluation of Three Different EEG Dry Electrode Types in Terms of Signal Spectral Features, Mental States Classification and Usability," Sensors 2019, 19 (1365): 1-21, 21 pages.
Emotiv, "Emotiv Epoc," retrieved from https://www.emotiv.com/epoc/, last visited Mar. 8, 2021, 12 pages.
Engelmann et al., "Individual differences in brain responses to cigarette-related cues and pleasant stimuli in young smokers," Drug Alcohol Depend. 2016, 163: 229-235, 7 pages.
Engelmann et al., "Neural substrates of smoking cue reactivity: a meta-analysis of fMRI studies," Neuroimage 2012, 60(1): 252-262, 30 pages.
Farwell, "Brain fingerprinting: a comprehensive tutorial review of detection of concealed information with event-related brain potentials," Cogn. Neurodyn. 2012, 6: 115-154.
Faulkner, "Beyond the five-user assumption: Benefits of increased sample sizes in usability testing," Behavior Research Methods, Instruments, & Computers 2003, 35(3): 379-383, 5 pages.
Fedoroff et al., "Evaluation of the Yale-Brown Obsessive Compulsive Scale (YBOCS-hd) for heavy drinking with mild to moderately dependent alcohol abusers," Alcohol. Clin. Exp. Res. 1999; 23(9): 1477-1483, 7 pages.
Frank et al., "Toward Precision Medicine for Smoking Cessation: Developing a Neuroimaging-Based Classification Algorithm to Identify Smokers at Higher Risk for Relapse," Nicotine & Tobacco Research 2019, 1-8, 8 pages.
Franken et al.., "Neurophysiological evidence for abnormal cognitive processing of drug cues in heroin dependence," Psychopharmacology 2003, 170: 205-212, 7 pages.
Garland et al., "Effects of Mindfulness-Oriented Recovery Enhancement on reward responsiveness and opioid cue-reactivity," Psychopharmacology 2014; 231: 3229-3238, 9 pages.
Garland et al., "Mindfulness-Oriented Recovery Enhancement reduces pain attentional bias in chronic pain patients," Psychother. Psychosom. 2013; 82(5): 311-318, 7 pages.
Garland et al., "Mindfulness-Oriented Recovery Enhancement remediates hedonic dysregulation in opioid users: Neural and affective evidence of target engagement," Sci. Adv. 2019, 5(eaax1569): 1-12, 13 pages.
Garland et al., Neurophysiological evidence for remediation of reward processing deficits in chronic pain and opioid misuse following treatment with Mindfulness-Oriented Recovery Enhancement: exploratory ERP findings from a pilot RCT, J. Behav. Med. 2015; 38: 327-336, 9 pages.
Gibney et al., "Estimating statistical power for event-related potential studies using the late positive potential," Psychophysiology 2019, retrieved from https://www.biorxiv.org/content/10.1101/574368v1, 34 pages.
Gloss et al.,"Practice advisory: The utility of EEG thera/beta power ration in ADHD diagnosis," Neurology 2016, 87: 2375-2379, 7 pages.
Goldstein, "Nonlinear multilevel models, with an application to discrete response data," Biometrika 1991, 78: 45-51, 7 pages.
Gu, "Incubation of craving: a Bayesian account," Neuropsychopharmacology 2018; 43: 2337-2339, 3 pages.
Haifeng et al., "P300 event-related potential in abstinent methamphetamine-dependent patients," Physiol. Behav. 2015, 149(1): 142-148, 6 pages.
Hendrikse et al., "Attentional biases for food cues in overweight and individuals with obesity: a systematic review of the literature, " World Obesity 2015, 16: 424-432, 9 pages.
Holla et al., "Brain Functional Magnetic Resonance Imaging Cue-reactivity Can Predict Baclofen Response in Alcohol Use Disorders, " Clin. Psychopharmacol. Neurosci. 2018, 16(3): 290-301, 11 pages.
Horndasch, "Cue reactivity towards bodies in anorexia nervosa - common and differential effects in adolescents and adults," Psychological Medicine 2018; 48(3): 508-18, 11 pages.
Ilgen et al., "Abstinence Self-Efficacy and Abstinence 1 Year After Substance Use Disorder Treatment," J. Consult. Clin. Psychol. 2005; 73(6): 1175-1180, 6 pages.
Janes et al., "Brain Reactivity to Smoking Cues Prior to Smoking Cessation Predicts Ability to Maintain Tobacco Abstinence," Biol. Psychiatry 2010, 67: 722-729, 8 pages.
Jasinska et al., "Factors modulating neural reactivity to drug cues in addiction: a survey of human neuroimaging studies," Neurosci. Biobehav. Rev. 2014; 38: 1-16, 35 pages.
Jiang et al., "Effect of Electro-acupuncture Intervention on Cognition Attention Bias in Heroin Addiction Abstinence-A Dot-probe-based Event-related Potential Study," Chin. J. Integr. Med. 2011, 17(4): 267-274, 5 pages.
Junghofer et al., " Fleeting images: A new look at early emotion discrimination," Psychophysiology 2001, 38: 175-178, 4 pages.
Karthik et al., "Alcohol-related cue-reactivity predicts abstinence duration in individuals with severe alcohol-use disorders," Eur. Psychiatry 2017; 41S: S877, 1 page.
Keil et al., "Committee report: Publication guidelines and recommendations for studies using electroencephalography and magnetoencephalography," Psychophysiology 2014; 51: 1-21, 21 pages.
Kim et al., "Increased Attentional Bias Toward Visual Cues in Internet Gaming Disorder and Obsessive-Compulsive Disorder: An Event-Related Potential Study," Frontiers in Psychiatry 2018; 9(315), 9 pages.
Koob et al., "Neurobiology of addiction: a neurocircuitry analysis," Lancet Psychiatry 2016, 3(8): 760-773, 28 pages.
Krigolson et al., "Choosing MUSE: Validation of a Low-Cost, Portable EEG System for ERP Research," Frontiers in Neuroscience 2017, 11(109): 1-10, 10 pages.
Kuhn et al., "Common biology of craving across legal and illegal drugs—a quantitative meta-analysis of cue-reactivity brain response," European J. of Neuroscience 2011; 33: 1318-1326, 9 pages.
Kurdi et al., "Introducing the Open Affective Standardized Image Set (OASIS)," Behav. Res. 2017, 49: 457-470, 14 pages.
Kwako et al., "Addiction Biomarkers: Dimensional Approaches to Understanding Addiction," Trends Mol. Med. 2018, 24(2): 121-128, 8 pages.
Kwako et al., "Addiction Neuroclinical Assessment: A Neuroscience-Based Framework for Addictive Disorders," Biol. Psychiatry 2016; 80(3): 179-189, 11 pages.
Li et al., "Predicting subsequent relapse by drug-related cue-induced brain activation in heroin addiction: an event-related functional magnetic resonance imaging study," Addict. Biol. 2014, 20: 968-978, 19 pages.
Littel et al., "Electrophysiological indices of biased cognitive processing of substance-related cues: A meta-analysis," Neuroscience and Biobehavioral Reviews 2012, 36: 1803-8016, 14 pages.
Liu et al., "Neural Substrate of the Late Positive Potential in Emotional Processing," J. Neurosci. 2012, 32(42): 14563-14572, 10 pages.
Lou et al., "Cue-elicited Craving in Heroin Addicts at Different Abstinent Time: An fMRI pilot study," Subst. Use & Misuse 2012, 47(6): 631-639, 10 pages.
Lubman et al., "Electrophysiological evidence that drug cues have greater salience than other affective stimuli in opiate addiction," J. Psychopharmacol. 2008, 22(8): 836-842, 7 pages.
Lubman et al., "Electrophysicological evidence of the motivational salience of drug cues in opiate addiction," Psychol. Med. 2007, 37: 1203-1209, 7 pages.
Lubman et al., "Responsiveness to drug cues and natural rewards in opiate addiction: associations with later heroin use, " Arch. Gen. Psychiatry 2009; 66(2): 205-213, 9 pages.
Luijten et al., "Event-related potentials reflecting smoking cue reactivity and cognitive control as predictors of smoking relapse and resumption," Psychopharmacology 2016, 233: 2857-2868, 12 pages.

(56) References Cited

OTHER PUBLICATIONS

Macniven et al., "Association of Neural Responses to Drug Cues With Subsequent Relapse to Stimuli and Use," JAMA Netw. Open 2018, 1(8): 1-14, 14 pages.
Magura et al., "Predictive Validity of the ASAM Patient Placement Criteria for Naturalistically Matched vs. Mismatched Alcoholism Patients," American J. on Addicts 2003, 12:386-397, 12 pages.
Makeig et al., "Evolving signal processing for brain-computer interfaces," Proceedings of the IEEE 2021, retrieved from http://dsp.ucsd.edu/~kreutz/Publications/makeig2012evolving.pdf, 51 pages.
Marini et al., "A comparative evaluation of signal quality between research-grade and wireless dry-electrode mobile EEG systems," J. Neural Eng. 2019, 1-34, 35 pages.
Martins et al., "Interactive Effects of Naturalistic Drinking Context and Alcohol Sensitivity on Neural Alcohol Cue-Reactivity Responses," Alcoholism: Clinical and Experimental Research 2019, 43(8): 1777-1789, 13 pages.
Matheus-Roth et al., "Occipital event-related potentials to addiction-related stimuli in detoxified patients with alcohol dependence, and their association with three-month relapse," BMC Psychiatry 2016, 16: 74-86, 12 pages.
McHugh et al., "Cue-Induced Craving to Paraphernalia and Drug Images in Opioid Dependence," The American Journal on Addiction 2016, 25: 105-109, 5 pages.
Miccoli et al., "Meet OLAF, a Good Friend of the IAPS! The Open Library of Affective Foods: A Tool to Investigate the Emotional Impact of Food in Adolescents," PLOS One 2014, 1-22, 22 pages.
Miller, "From Volume To Value: Better Ways to Pay for Health Care," Health Aff. 2009; 28: 1418-1428, 11 pages.
Mullen et al., "Real-Time Neuroimaging and Cognitive Monitoring Using Wearable Dry EEG," IEEE Trans. Biomed. Eng. 2015, 62(11): 2553-2567, 40 pages.
Nunes et al., "Relapse to opioid use disorder after inpatient treatment: Protective effect of injection naltrexone," J. Subst. Abuse Treat. 2018, 85: 49-55, 17 pages.
Owens et al.,"Neural correlates of tobacco cue reactivity predict duration to lapse and continuous abstinence in smoking cessation treatment," Addict. Biol. 2018, 23: 1189-1199, 11 pages.
Palmieri et al., "Lies in the doctor-patient relationship," Prim. Care Companion J. Clin. Psychiatry 2009; 11(4): 163-168, 6 pages.
Parvaz et al., "Abstinence reverses EEG-indexed attention bias between drug-related and pleasant stimuli in cocaine-addicted individuals," J. Psychiatry Neurosci. 2017, 42(2):78-86, 9 pages.
Parvaz et al., "Incubation of Cue-Induced Craving in Adults Addicted to Cocaine Measured by Electroencephalography," JAMA Psychiatry 2016; 73(11): 1127-1134, 8 pages.
Paulus et al., "The role of interoception and alliesthesia in addiction," Pharmacol. Biochem. Behav. 2009; 94: 1-7, 7 pages.
Petit et al., "Reduced processing of alcohol cues predicts abstinence in recently detoxified alcoholic patients in a three-month follow up period: An ERP study," Behavioral Brain Research 2015, 282: 84-94, 11 pages.
Pickens et al., "Neurobiology of the incubation of drug craving," Trends Neurosci. 2011; 34(8): 411-20, 10 pages.
Proctor et al., "The continuing care model of substance use treatment: what works, and when is 'enough,' enough'?," Psychiatry J. 2014, 1-16, 17 pages.
Raduntz, "Signal Quality Evaluation of Emerging EEG Devices," Frontiers in Physiology 2018; 9(98): 1-12, 12 pages.
Ries et al., "A Comparison of Electroencephalography Signals Acquired from Conventional and Mobile Systems," J. of Neuroscience and Neuroengineering 2014, 3: 10-20, 12 pages.
Robinson et al., "Incentive-sensitization and addiction," Addiction 2001; 96: 103-114, 12 pages.
Robinson et al., "The neural basis of drug craving: an incentive-sensitization theory of addiction," Brain Res. Rev. 1993, 18: 247-91, 45 pages.
Sabatinelli et al., "Emotional perception: correlation of functional MRI and event-related potentials," Cereb. Cortex 2007, 17: 1085-1091, 7 pages.
Saunders et al., "Individual variation in resisting temptation; implications for addiction," Neurosci. Biobehav. Rev. Nov. 2013; 37(0), 49 pages.
Schacht et al., "Functional neuroimaging studies of alcohol cue reactivity: a quantitative meta-analysis and systematic review," Addict. Biol. 2013; 18(1): 121-133, 23 pages.
Schupp et al., "The selective processing of briefly presented affective pictures: an ERP analysis," Pscyhophysiology 2004, 41: 441-449, 9 pages.
Schupp et al.,"Affective picture processing: the late positive potential is modulated by motivational relevance," Pscyhophysiology 2000, 37: 257-261, 5 pages.
Silva et al., "Biophysical Aspects of EEG and MEG Generation," Niedermeyer's Electroencephalography, Oxford University Press, 12 pages.
Smith et al., "Regression-based estimation of ERP waveforms: I. The rERP framework," Psychophysiology 2015, 52 (2): 157-168, 26 pages.
Smith et al., "Regression-based estimation of ERP waveforms: II. Nonlinear effects, overlap correction, and practical considerations," Psychophysiology 2015, 52:169-181, 13 pages.
Smyth et al., "Lapse and Relapse Following Inpatient Treatment of Opiate Dependence," Ir. Med. J. Jun. 2010; 103 (6): 176-9, 1 page.
Swan, "The Quantified Self: Fundamental Disruption in Big Data Science and Biological Discovery," Big Data 2013, 1 (2):85-99, 15 pages.
Tomie et al., "Behavioral Characteristics and Neurobiological Substrates Shared by Pavlovian Sign-Tracking and Drug Abuse," Brain Res Rev. 2008; 58(1): 121-135, 15 pages.
Verdejo-Garcia et al., "A Roadmap for Integrating Neuroscience Into Addiction Treatment: A Consensus of the Neuroscience Interest Group of the International Society of Addiction Medicine," Fron. Psychiatry 2019; 10: 877, 23 pages.
Verdejo-Garcia et al., "The role of interoception in addiction: a critical review," Neurosci. Biobehav. Rev. 2012, 36: 1857-1869, 13 pages.
Versace et al., Beyond cue reactivity: blunted brain responses to pleasant stimuli predict long-term smoking abstinence, Addict. Biol. 2012; 17: 991-1000, 10 pages.
Versace et al., "Beyond Cue Reactivity: Non-Drug-Related Motivationally Relevant Stimuli Are Necessary to Understand Reactivity to Drug-Related Cues," Nicotine & Tobacco Research 2017, 663-669, 7 pages.
Versace et al., "Brain Responses to Cigarette-Related and Emotional Images in Smokers During Smoking Cessation: No Effect of Varenicline or Bupropion on the Late Positive Potential," Nicotine & Tobacco Research 2019, 234-240, 7 pages.
Versace et al., "Heterogeneity in brain reactivity to pleasant and food cues: evidence of sign-tracking in humans," Soc. Cogn. Affect. Neurosci. 2016; 11: 604-611, 8 pages.
Versace et al., "Prequit fMRI responses to pleasant cues and cigarette-related cues predict smoking cessation outcome," Nicotine Tob. Res. 2014, 16: 697-708, 12 pages.
Versace et al., "The reality of 'food porn': Larger brain responses to food-related cues than to erotic images predict cue-induced eating," Psychophysiology 2019; 56: e13309, 13 pages.
Virzi, "Refining the Test Phase of Usability Evaluation: How Many Subjects Is Enough?" Human Factors 1992, 34(4): 457-468, 12 pages.
Widge et al., "Electroencephalographic Biomarkers for Treatment Response Prediction in Major Depressive Illness: A Meta-Analysis," Am J Psychiatry 2019, 176(1):44-56, 13 pages.
Wilcox et al., "Default mode network deactivation to smoking cue relative to food cue predicts treatment outcome in nicotine use disorder," Addict. Biol. 2018, 23: 412-424, 13 pages.
Witbrodt et al., "Day Hospital and Residential Addiction Treatment: Randomized and Nonrandomized Managed Care Clients," J. of Consulting and Clinical Psychology 2007, 75(6): 947-959, 13 pages.
Witkiewitz et al., Mindfulness-based relapse prevention for alcohol and substance use disorders, J. Cogn. Psychother. 2005, 19(3): 211-228, 19 pages.

(56) References Cited

OTHER PUBLICATIONS

Wu et al., "An Electroencephalographic signature predicts antidepressant response in major depression," Nature Biotechnology 2020, 38: 439-447, 20 Pages.

Zuckerman et al., "Development of a Sensation-Seeking Scale," J of Consulting Psychology 1964, 28(6): 477-482, 6 pages.

Picton et al., "Guidelines for using human event-related potentials to study cognition: Recording standards and publication criteria," Psychophysiology 2000; 37(2000):127-152, 26 pages.

Muse, "Neurofeedback EEG Device—How it Works," retrieved from https://choosemuse.com/how-it-works/, last visited Oct. 26, 2021, 8 pages.

Koob et al., "Neurocircuitry of Addiction," Neuropsychopharmacology Reviews 2010, 35: 217-238, 22 pages.

Fazei-Rezai et al., "P300 brain computer interface: current challenges and emerging trends," Frontiers in Neuroengineering 2012, 5(14): 1-14, 14 pages.

Carter et. al., "Meta-analysis of cue-reactivity in addiction research," Addiction 1999, 94(3): 327-240, 15 pages.

Jiang et al., "Effect of Electro-acupuncture Intervention on Cognition Attention Bias in Heroin Addiction Abstinence-A Dot-probe-based Even-related Potential Study, "Chin. J. Integr. Med, 2011, 17(4): 267-274, 5 pages.

Neurosity, "Crown," retrieved from https://neurosity.co/, last visited Oct. 28, 2021, 2 pages.

Ravi, "Train your Mind and Free your Code," retrieved from https://medium.com/an-idea/train-your-mind-and-free-your-code-5bd635b91ebb, last visited Oct. 28, 2021, 5 pages.

Neurosity, "Notion 2," retrieved from https://neurosity.co/, last visited Mar. 8, 2021, 6 pages.

\* cited by examiner

ASSESSING MOTIVATED ATTENTION WITH CUE REACTIVITY

CROSS-REFERENCE TO RELATED APPLICATIONS

This application claims the benefit of U.S. Provisional Application Ser. No. 63/010,042, titled "Mobile Brain Sensing Platform for Detection of Opioid Craving and Treatment Response," filed on Apr. 14, 2020, and U.S. Provisional Application Ser. No. 63/010,040, titled "Assessing Cue Reactivity," filed on Apr. 14, 2020.

This application incorporates the entire contents of the foregoing application(s) herein by reference.

BACKGROUND

A critical challenge in treating behavioral disorders like drug and alcohol addictions is a lack of tools to inform treatment and prevent problems from recurring after initial recovery has been successful, such as relapse (resumption of symptoms or disorder) following prolonged abstinence. Lapse (resumed engagement of addictive behaviors) or relapse in drug and alcohol addictions are especially dangerous because of potential overdoses and death. For example, in opioid addictions, even a single dose after a period of detoxification and abstinence carries a risk of fatal overdose.

SUMMARY

In some implementations, a system includes a portable computing device having (a) a graphical user interface for displaying images, (b) a device transceiver, and (c) a computing device processor; and a portable electroencephalographic (EEG) headset having (i) a plurality of electrodes configured to capture electrical neural signals of a user wearing the portable EEG headset, (ii) signal processing circuitry configured to create digital information from the captured electrical neural signals; (iii) a headset processor, and (iv) a headset transceiver configured to exchange information with the device transceiver.

Either or both of the computing device processor and the headset processor may execute instructions to display a sequence of images on the graphical user interface; receive the digital information, in a time-synchronized manner relative to the displayed sequence of images; extract from the digital information, one or more event-related potential (ERP) peaks associated with each image in the sequence of images; quantify one or more affect-related measures associated with the one or more ERP peaks, each affect-related measure comprising a pleasantness aspect and an intensity aspect; and compare the quantified one or more affect-related measures to baseline data to determine risk to a user of the portable EEG headset of (i) a proclivity to a maladaptive behavior or substance use or (ii) relapse to use of a substance or engagement in a behavior.

The system may further include a centralized computing facility having a data store and being coupled to the portable computing device by a network, through the device transceiver. The data store may store the baseline data.

In some implementations, a system includes a portable electroencephalographic (EEG) headset, configured to capture user EEG signals; a computing device having a graphical user interface; and one or more processors. The one or more processors may execute instructions to display a sequence of images on the graphical user interface; receive, from the portable EEG headset, user EEG signals that are time-synchronized with the display of the sequence of images; extract from the user EEG signals, one or more event-related potential (ERP) peaks associated with each image; quantify one or more affect-related measures associated with the one or more ERP peaks; and compare the quantified one or more affect-related measures to baseline data to determine a risk to the user.

Risk to the user may include one of a proclivity to a maladaptive behavior or substance use, or a relapse to use of a substance or engagement of a behavior. Quantifying one or more affect-related measures may include quantifying a pleasantness or an intensity. Quantifying a pleasantness or an intensity may include determining whether the one or more ERP peaks are above a first threshold or below a second threshold.

Quantifying one or more affect-related measures may include determining a semantic content associated with each image, and that semantic content may be directly relevant to a user's risk (e.g., drug-related for drug addiction) or irrelevant (e.g., non-drug-related) to a user's risk.

The first threshold and second threshold may be characterized with reference to an electrode on the portable EEG headset. The first threshold and second threshold may be further characterized with reference to a normative population distribution. At least one of the first threshold or second threshold may correspond to population-based expected values based on normative ratings of affective pleasantness and intensity of a corresponding image. The first threshold and second threshold may be further characterized with reference to historical data associated with a user of the EEG headset.

Extracting one or more ERP peaks associated with an image may include identifying a peak or trough within a specified period of time relative to display of the image on the graphical user interface. The specified period of time may be within a range of approximately 600 milliseconds to 1000 milliseconds, approximately 400 milliseconds to 1500 milliseconds, or approximately 150 milliseconds to 1500 milliseconds.

Comparing the quantified one or more affect-related measures to baseline data may include comparing an average of multiple individual ERP peaks associated with a category of risk-relevant (e.g., drug-related) images to an average of multiple ERP peaks associated with categories of neutral or affect-related images.

In some implementations, a method of treating a user for an addictive or motivational salience disorder includes displaying to the user a first sequence of images; capturing from the user, with a portable electroencephalographic (EEG) headset and in a time-synchronized manner relative to displaying the first sequence of images, a set of baseline event-related potential (ERP) peaks associated with the first sequence of images; delivering a first type of therapy to the user; subsequent to delivering the first type of therapy for a period of time, displaying to the user a second sequence of images; capturing from the user, with the portable EEG headset and in a time-synchronized manner relative to displaying the second sequence of images, a set of intermediate-treatment ERP peaks associated with the second sequence of images; determining a change of the intermediate-treatment ERP peaks relative to the baseline ERP peaks; and when the change exceeds a threshold value, delivering a second type of therapy that is different than the first type of therapy; and if the change does not exceed the threshold value, continuing to deliver the first type of therapy.

Capturing either the baseline ERP peaks or the intermediate-treatment ERP peaks may include (a) receiving EEG signals from the portable EEG headset, (b) extracting ERP peaks from the received EEG signals, and (c) quantifying the extracted ERP peaks with affect-related measures having a pleasantness aspect and intensity aspect. Quantifying the extracted ERP peaks with affect-related measures may include determining whether the extracted ERP peaks are above a first threshold or below a second threshold. At least one of the first threshold or second threshold may corresponds to a population-level expected value that is determined based on normative rating of affective pleasantness and intensity for a corresponding image.

The first type of therapy may include at least one of a pharmaceutical treatment therapy, a psychological or behavior modification therapy, or a neuromodulation treatment. The second type of therapy may include displaying to the user a report, graph, or chart of historical change in affect-related measures of the user's physiological response to images in the first sequence or the second sequence.

DETAILED DESCRIPTION

Pavlovian Conditioning

Figure 1:
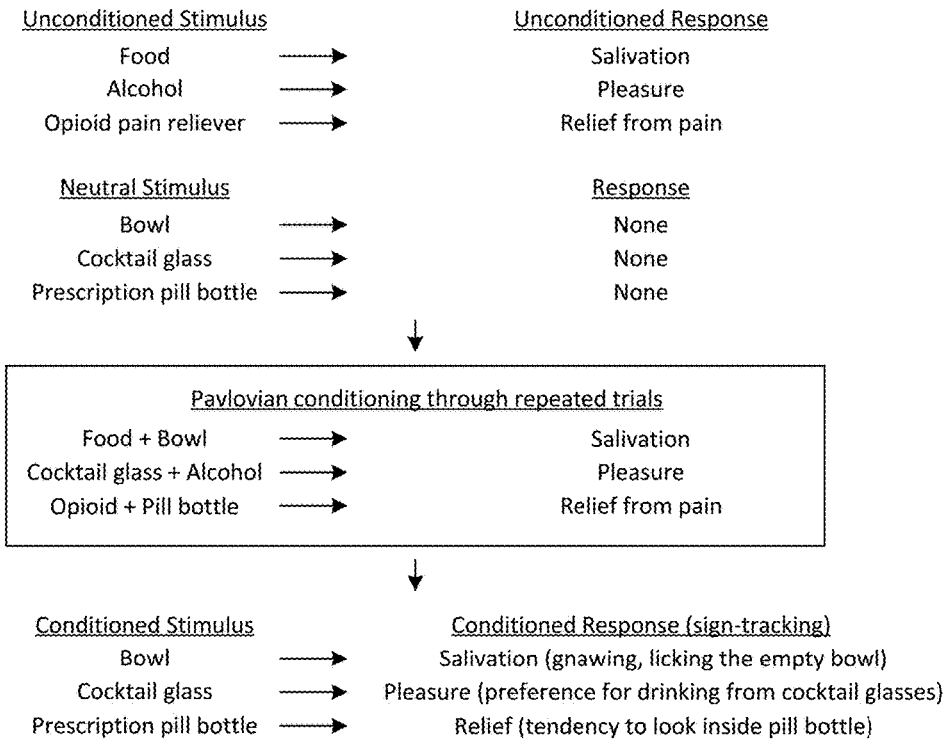
FIG. 1 illustrates a process of Pavlovian conditioning.

As Pavlov demonstrated over a century ago, when what starts out as a neutral stimulus comes to reliably predict (e.g., through association with) the delivery of a naturally rewarding or punishing stimulus, presentation of the neutral stimulus can, over time, come to elicit a response that was previously associated with the reward or punishment itself. In Pavlov's experiments involving dogs, food, and the bowls used to hold the food, an "unconditioned stimulus" (food by itself) was provided, causing an "unconditioned response" (salivation on the part of the dog). During conditioning, an otherwise "neutral stimulus" (the bowl) was repeatedly presented alongside delivery of the food, again causing the unconditioned response (salivation on the part of the dog). Over time, though, presentation of the bowl alone came to predict salivation from the dog. This process, whereby a "conditioned stimulus" (a neutral stimulus—here, a bowl—that has been repeatedly paired with an unconditioned stimulus) causes a "conditioned response" (here, salivation), is widely referred to as Pavolovian conditioning.

In some types of Pavlovian conditioning, a conditioned stimulus may also elicit a "draw" or approach response, which in the case of Pavlov's dogs came in the form of gnawing, licking, chewing, or other attempts to "consume" the empty bowl despite it having no inherent rewarding or satiating properties. This conditioned approach response may be referred to as "sign-tracking" (also called "autoshaping"), and because its occurrence does not necessarily result in the delivery of food (or any other unconditioned stimuli), it serves no instrumental purpose to the animal. Rather, sign-tracking often results in non-instrumental performance of instrumental-type responding, as exerting effort and time on trying to consume the conditioned stimulus wastes the time and energy of the animal that could otherwise be spent on attempting to attain actual rewards (e.g., unconditioned stimulus). "Sign-tracking," thus is considered a maladaptation to the more normal "goal-tracking," whereby the draw is predominantly formed to the natural reward (e.g., the food, in the case of Pavlov's dogs) instead of the conditioned stimulus (the bowl).

Sign-Tracking as it Relates to Incentives and Motivational Salience

In conditioning and sign-tracking, the "draw," or perceptual properties of a given stimulus or event that make it attention-grabbing and wanted is referred to as "incentive salience." A stimulus or event that possesses incentive salience likely activates the brain's reward systems, making it "stand out" and attractive relative to other stimuli or events. Incentive salience for a particular stimulus or event might occur because of unconditioned reasons (e.g., the stimulus or event is evolutionarily relevant, such as food or sex), or it may be acquired through conditioning. Importantly, incentive salience reflects an anticipatory response to stimuli and events and confers "desire" or "want" to engage with the stimulus or event, rather than the actual "pleasure" or "liking" that occurs once the engagement has commenced.

Incentive salience occurs within the broader context of "motivational salience," which refers to both perception of appetitive/rewarding (e.g., pleasure) and avoidant/aversive (e.g., pain) properties for a given stimulus or event, and may motivate or propel an individual's behavior towards or away from (respectively) the stimulus or event. The degree of motivational salience attributed to a stimulus or event regulates the intensity of approach or avoidant behaviors and the associated psychological and physiological processes. To the extent that motivational salience of conditioned stimuli or events drives behavioral, psychological, and physiological processes, sign-tracking may be said to occur.

Addictive Behaviors, Pavlovian Conditioning, and Sign-Tracking

Addictive behaviors (and other behaviors associated with disorders like major depressive disorder (MDD) or post-traumatic stress disorder (PTSD)) may be in part explained by conditioning and incentive salience principles which may manifest sign-tracking. For example, with reference to FIG. 1, repeated alcohol consumption accompanied by alcohol's rewarding effects (e.g., pleasure) may result in conditioning of approach behavior towards stimuli and situations frequently accompanying the drinking (e.g., preferring to drink liquids from cocktail glasses relative to other glasses, preferring to spend time in taverns instead of other places), which engagement with by itself (i.e., the cocktail glass sans alcohol) is not sufficient to deliver the reward (i.e., alcohol's rewarding effects), but nonetheless situate the individual imminently close to the addictive behavior (i.e., consuming alcohol). Similarly, if a person suffering from chronic pain obtains relief from ingesting a prescription opioid pain reliever capsule, an otherwise neutral stimulus (e.g., a prescription pill bottle) may itself become an attractive cue and induce approach behaviors such as opening the pill bottle to view its contents, regardless of whether there exist opioid pills on the inside. Importantly, the presence and magnitude of such conditioned responses and sign-tracking may occur independently of the actual pleasure experienced by re-engagement with the unconditioned stimulus, such as experiencing psychoactive effects of drinking alcohol or taking opioids, which may explain why a person with an addiction may continue to engage addictive behaviors without reporting any pleasure from those engagements.

Hedonic Regulation and Dysregulation

Sign-tracking may be thought of as a disruption in normal hedonic regulation, the pursuit of normal or unconditioned pleasurable experiences and avoidance of aversive experiences. For example, a normal hedonically regulated individual will seek natural pleasure-eliciting activities (e.g., consumption of high caloric foods, sex) and stop pursuing them after they are obtained, and the individual is satiated. On the other hand, in people with hedonic dysregulation, such normal hedonic processes are compromised, and an individual may be drawn towards, or engaged in weakened avoidance of, harmful experiences. Alternatively, hedonic dysregulation may occur when an individual pursues experiences that may not be naturally pleasurable and/or yield diminished satiation once completed.

Some individuals with drug or alcohol addictions exhibit hedonic dysregulation. For example, such individuals may have an exaggerated focus on drug-seeking relative to their pursuit of natural rewards such as a healthy lifestyle and prosocial behaviors. One leading theory, in line with incentive salience processes, is that while the "liking" associated with taking drugs diminishes over repeated uses (e.g., through increased tolerance), the "wanting" may persist, and thus the individual seeks drug use despite such diminished returns.

Impulsivity may also influence addiction tendencies. A tendency towards impulsive behaviors, defined here as carrying out a certain act upon being presented with a certain stimulus or event (e.g., flipping "on" a light switch upon seeing it when first entering a room regardless of whether the room is already illuminated), rather than acting in the service of achieving a certain goal (e.g., wanting illumination in the room, and then flipping the light switch "on"), may put an individual at higher risk of developing or maintaining an addiction. For example, early on, before an addiction fully develops, taking of drugs or alcohol may be viewed as an impulsive act for some people: the potentially addictive behavior is engaged in without a clear goal or outcome intended, e.g., drinking alcohol because a beverage is in one's hand, and not because one seeks the pleasurable effects. However, after an addiction has developed, this impulsivity may give way to more compulsive (i.e., craving- or stress-driven) drug or alcohol use, which may involve neurobiological adaptations.

Conditioned cues may motivate maladaptive patterns of hedonic dysregulation and behavior in some individuals more than others; that is, some individuals may have more difficulty in resisting the temptation to seek out and consume food or drugs that have previously been experienced as rewards, when those individuals are faced with cues, such as a sights, sounds, smells and places associated with the rewards. In short, similar to impulsivity driving a "stimulus-action" behavioral pattern, increased "cue reactivity" may make an individual especially vulnerable to sign-tracking and its downstream consequences, such as actually engaging in the addictive behavior upon encountering the conditioned cue(s).

Addictions Generally

There are several ways in which aberrant motivational salience may develop, and they are not limited to drug or alcohol addictions. For example, so-called "behavioral addictions" to mobile phone use or social media engagement, exercise, gaming or gambling, internet use, relationships, shopping, pornography, etc. are possible. Additionally, aberrant motivational salience and sign-tracking may be involved in over-engagement of typically normal hedonic behaviors. For example, overeating and obesity may be linked to exaggerated incentive salience of high caloric/food-related stimuli; pathological gambling may be linked to exaggerated incentive salience of stimuli reflecting a scarce resource such as money and wealth; hypersexuality and pornography addiction may be linked to exaggerated incentive salience to stimuli representing sex or companionship. On the other hand, post-traumatic stress disorder may be linked to aversive salience of stimuli reflecting a previous traumatic experience, or a specific phobia may be linked to aversive salience of stimuli reflecting a stimulus or event for which an individual harbors extreme avoidance (e.g., bridge, heights). Other abnormalities in motivational salience may explain other psychopathological symptoms where over-engagement or over-avoidance is typical, such as obsessive-compulsivity, restricted eating, mental rumination, delusions, habits, etc.

Such addictive behaviors frequently co-occur with other types of psychological and behavioral disorders: alcohol addictions often co-occur with antisocial behavior; eating disorders often co-occur with depression and anxiety, to name a couple. Despite differences in taxonomy, the psychological and physiological processes underlying different addictions and other co-occurring disorders frequently overlap and may be linked to core processes of cue reactivity, motivational salience, and sign-tracking.

Approaches to Therapy

Various therapies may be applied to different addiction and disorders of motivational salience. Behavioral and psychological therapy (e.g., counseling) may be used to help restore balance in behavioral and mental health. For example, for drug addictions, behavioral therapies may directly target restoring normal behavioral and perceptual processes with regards to environmental cues: e.g., some therapies focus on enhancing the perceived incentive salience of natural or healthy rewards; others, such as "exposure-related" therapies applied to incentive or aversive salience, might focus on decreasing the motivational salience of drug-related or stress-provoking cues. So-called Cognitive-Behavioral Therapy may be applied in group or individual sessions that are designed to assist patients in recognizing, avoiding and coping with cues or situations in which they may be likely to engage in problematic addictive behaviors. Such approaches may also use Mindfulness-Based Therapy techniques to focus one's attention, thoughts, and feelings without placing judgments upon them. Contingency management uses positive reinforcement (e.g., rewards or privileges) to encourage freedom from drugs. Motivational enhancement therapy may apply strategies to capitalize on a patient's readiness to change behavior. Family therapy can help patients and their families identify and address influences toward maladaptive behavior, such as drug use. Additionally, using biofeedback or neuromodulation (e.g., magnetic, electrical, optical, or genetic brain stimulation, etc.) alone or in conjunction with such therapies may help decrease unpleasant motivational states (e.g., craving, anxiety) and/or increase inhibitory control over addictive behaviors.

Depending on the addictive agent (e.g., nicotine, opioids, alcohol, etc.), medication may also help prevent craving and subsequent lapse or relapse during recovery. Such medications may support the restoration of normal emotion and cognition while other therapy techniques are applied to attempt to manage addictive behaviors.

Relapse

One common goal of effective therapy is to reduce recurrence of problematic behaviors or relapse. Depending on the patient population, addictive agent of interest (e.g., nicotine, opioid, alcohol, etc.), and other treatment factors, lapse and relapse occur frequently, often in around 50% to 90% of patients in as few as 30 days after successful treatment completion. Medication, more intense or longer-duration treatments, or other adjunctive therapies may decrease the likelihood of relapse, but no known strategy works for all cases.

One crucial and frequently acknowledged shortcoming of current treatment is that knowing whether a person will re-develop recurrent problems (e.g., lapse or relapse) after they complete treatment is very difficult; in other words, measurement of a patient's symptoms in a treatment setting may poorly predict how that patient will fare in a non-treatment setting, days, weeks, or months after the patient has successfully completed treatment and has been discharged. Vulnerability for recurrent problems may be greatest weeks or months into recovery, and this vulnerability may occur without conscious awareness to the patient in recovery or to the patient's health care providers. For example, while a patient with a drug addiction may report relatively mild subjective feelings or interest to resume drug use at the clinic or point of care, other measures of objective reactivity to drug-related cues (which may not be currently measured in such settings—such as physiological readings, etc.) may still be severely high.

When addiction-related cues are perceived with incentive salience, they can facilitate lapse and relapse in several ways. First, such cues may elicit motivated attention bias (i.e., drug-related cues draw increased "focus" of the viewer relative to non-drug-related stimuli) which in turn can encourage approach behaviors (e.g., seeking drug-associated places and paraphernalia). Second, because interaction with incentive salient cues engages the brain's reward circuitry, interaction with such cues is reinforcing and thus likely to be repeated. Finally, incentive salient cues can bring about a conditioned motivational feeling or state, such as subjective drug wanting or craving.

Cues associated with drugs can elicit incentive salience processes for very long periods, which may be measured from behavior or neurobiological assays. For example, cue-induced approach behaviors in humans and animals with acquired excessive cocaine taking has been shown to be heightened over the several weeks of abstinence and remains elevated for an extended period of time. Lapse and relapse then, is precipitated by approach towards such cues, and resumption of the problematic addictive behavior naturally follows in succession.

Figure 2:
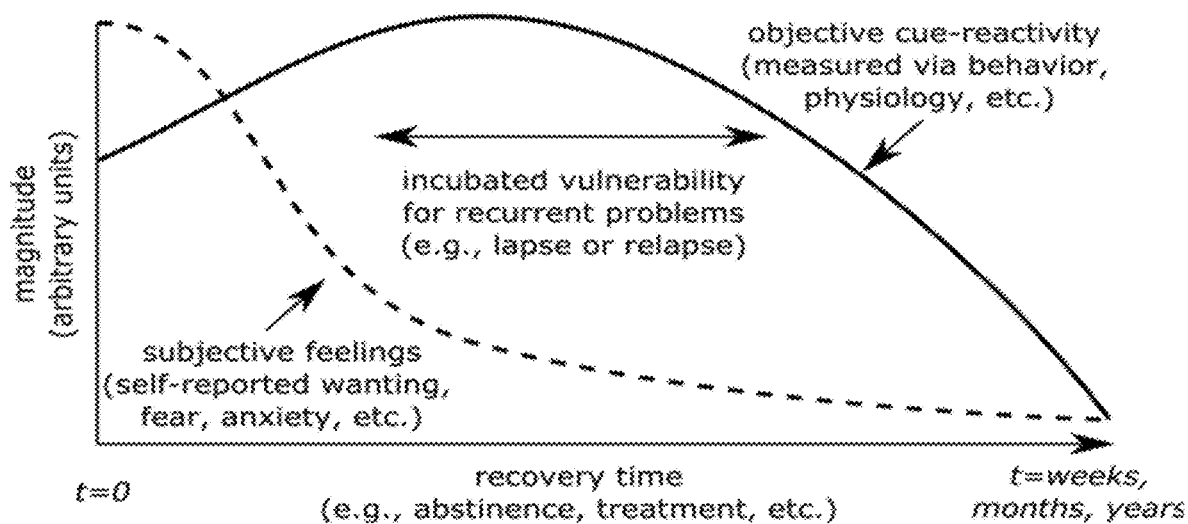
FIG. 2 illustrates an exemplary trajectory of self-reported craving and objective cue-reactivity of a person in addiction recovery.

Craving—a Precursor to Lapse and Relapse: Motivational Salience and Attention Bias Craving, defined here as a subjective experience (e.g., feeling) of wanting to engage in a particular addictive behavior, is a highly potent psychological antecedent for lapse and relapse. Research has shown that cue-induced self-reported subjective craving—e.g., presenting a drug-addicted person with drug-related cues or paraphernalia during abstinence and asking them how much they "want" the drug—increases in short-term abstinence (e.g., hours or days) and declines steadily over long-term abstinence (e.g., weeks, months, or years) (see FIG. 2). On the other hand, objective measures of incentive salience (e.g., drug-related cue reactivity and/or sign-tracking) obtained by quantifying physiological or approach behavioral responses to drug cues may follow a more protracted, and nonlinear (e.g., inverted-U) trajectory over weeks, months, or years. One's vulnerability to relapse then, as evidenced by these objective cue reactivity measures, may be substantially higher than subjective, self-reported assessments of craving in several weeks and months of abstinence; and the apex may be particularly large even several weeks or months into abstinence, when many people going through addiction recovery are vulnerable to relapse.

Studies have shown considerable individual variation in how drug-related cues elicit objective measures of cue reactivity. Not all individuals are tempted to consume drugs in a maladaptive way—for example, only a subset of the general population develops an addiction to drugs or alcohol, even though a large portion of that general population uses potentially addictive substances at different points in their lives. The degree to which humans find drug cues attractive, as measured by the degree to which such cues can bias motivational attention relative to neutral cues, predicts craving for drugs, prospective drug use and relapse. Studies show a direct correlation between the attractiveness and attention-grabbing nature of drug cues and the drug cues' ability to motivate drug use.

Some studies show that manipulating motivational attentional bias to drug cues through attentional control therapies may be effective in reducing the powerful effect of drug cues to addicts. Subjective measures of craving may be used clinically to assess treatment outcome, e.g., before, during, or after treatment. Such measures may employ patient-reported surveys, and/or they may include the use of pictorial stimuli to elicit objectively measurable emotional responses. However, for reasons noted with reference to FIG. 2, subjective measures of craving may not be reliable predictors of relapse.

Image Viewing for Investigating Brain Responses; EEGs and ERPs

One method by which scientists may objectively investigate motivational salience and attentional bias is through an image-viewing paradigm that enables quantifying physiological responses to affective (i.e., motivationally relevant) stimuli. Such a set of photographic images may contain animals, objects, people, scenes or other emotion-laden content, and each image is accompanied by "typical" ratings obtained by prior surveys in normal populations; these affective ratings include at least a dimension of affective "valence" or "pleasantness" (e.g., "how pleasant an emotion does the image elicit?"; on a scale ranging from "very unpleasant" to "very pleasant," with "neutral" in the middle) and another dimension of affective "intensity" or "arousal" (e.g., "how much emotional arousal is elicited by the image?"; on a scale of "very low" to "very high," with "neither low nor high" in the middle) by a normative reference group.

Relative to subjective (e.g., self-report) measures, studies measuring electroencephalographic (EEG) brain responses to images with affective content may provide a more objective way to quantify cue-induced motivated attentional biases than self-reported assessments of craving. These EEG responses are generally referred to as event-related potentials (ERPs)—voltage fluctuations that are time-locked to discrete events (e.g., presentation of a visual stimulus, pressing of a button, etc.) and reflect preparatory, perceptual, or other cognitive processes. ERPs are often measured by the latency (timing) and amplitude (size) of their peaks (hereinafter, the term "peak" may refer to either a positive- or negative-going peak or trough), which vary depending on the nature of the event that elicited them (e.g., stimulus or task properties) and individual differences (e.g., person with an addiction vs. person without an addiction).

Figure 3:
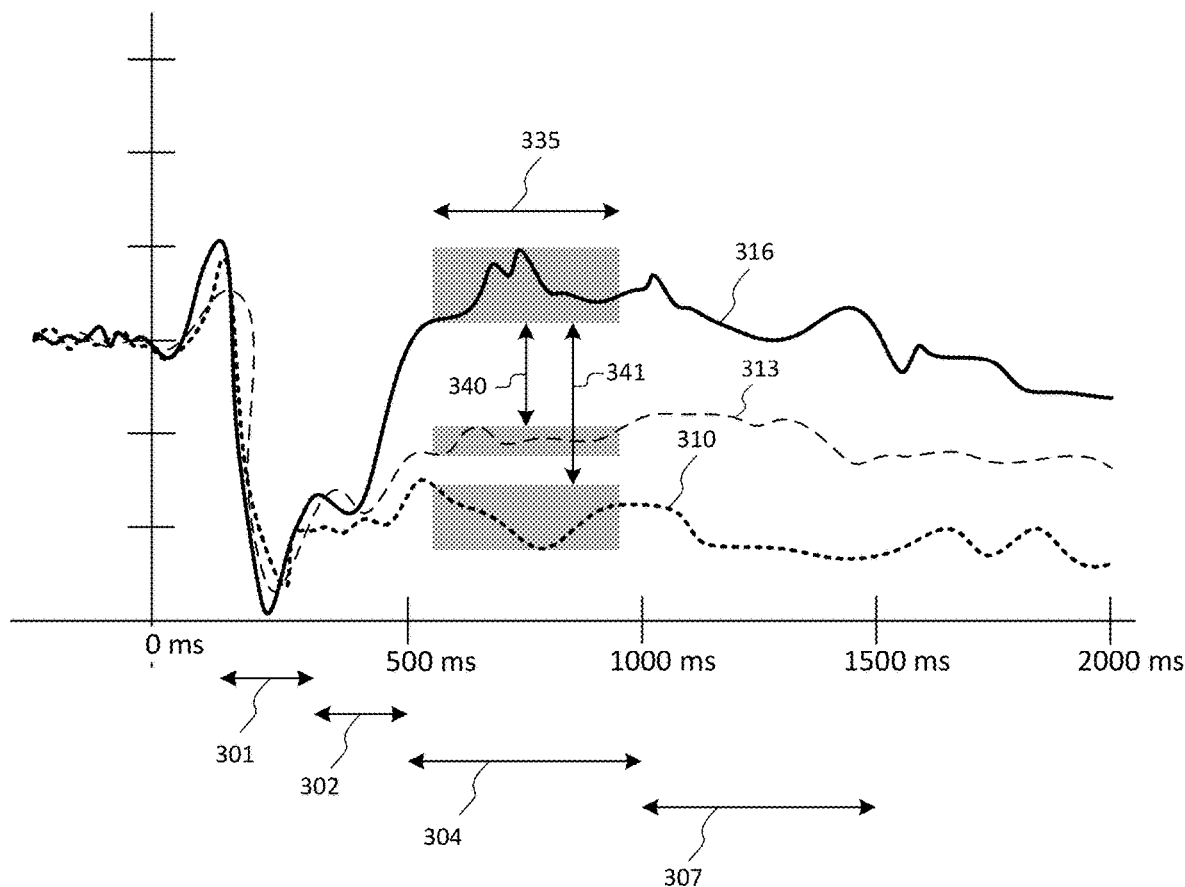
FIG. 3 depicts stylized exemplary event-related potential (ERP) signals following presentation of a visual stimulus.

FIG. 3 depicts stylized ERPs based on typical recordings, corresponding to presentation of a visual stimulus (e.g., an affective image) at t=0 milliseconds. Three commonly studied ERP peaks are the early posterior negativity (EPN—a large negative deflection of the ERP, about 150 to 300 milliseconds after stimulus presentation, during period 301), P300 (or "P3"—a large positive deflection of the ERP, about 300-500 milliseconds after stimulus presentation, during period 302), and the late positive potential (LPP), which typically reaches a maximum amplitude between 500 and 1000 milliseconds (period 304) after image presentation and remains significantly larger for affectively intense stimuli, often lasting to 1000-1500 milliseconds (period 307).

The amplitude of the LPP is theorized to reflect sustained, motivated attention, and this makes it a good candidate assay for measuring motivational salience and attention bias. As such, the amplitudes of LPP measurements are larger as the affective intensity of the images used to elicit it increases. For example, signal 310 may correspond to an ERP elicited by presentation of an image having neutral valence (neither pleasant nor unpleasant) and low affective intensity ratings; whereas signal 313 may correspond to the ERP elicited by presentation of an image characterized by high affective intensity content; and signal 316 may correspond to the ERP elicited by presentation of an image characterized by higher still affective intensity content.

Cues with perceived motivational salience to the viewer elicit greater attentional processes (e.g., EPN, P3, and/or LPP) relative to other cues. For an individual without a drug addiction, images of affectively intense content (e.g., chocolate cake or a venomous spider) may possess motivational salience and thus elicit high attentional processes, whereas images of ordinary medical supplies (e.g., syringe, pill bottle) or household supplies (e.g., highlighter marker, tape dispenser) objects typically do not. However, for an individual with an addiction to opioid drugs, some opioid drug-related paraphernalia (e.g., syringe or pill bottle) may carry incentive salience, and thus elicit abnormally high attentional processes and large ERP peaks.

Referring to FIG. 3, in a person without a drug addiction, the signal 310 may reflect a normal/expected ERP elicited by an image with neutral valence (regardless of whether the image is drug-related), signals 313 and 316 may correspond to normal/expected ERPs elicited by moderately and very pleasant cues (respectively), or moderately and very unpleasant cues (respectively). However, in an individual with an opioid drug addiction, while a non-drug-related image with neutral valence (e.g., highlighter pen, tape dispenser) may elicit a small amplitude ERP such as signal 310, a drug-related image (despite its neutral valence, e.g., syringe, pill bottle) may elicit a larger amplitude ERP such as signal 316. Similar patterns may be observed with other addictive behaviors and stimuli.

Moreover, for an individual with a drug addiction, a drug-related image may elicit an ERP of large amplitude (e.g., signal 316) that is substantially larger than the ERP elicited by high pleasantness/affective intensity images (e.g., signal 313). Larger amplitude ERP peaks in the person with a drug addiction is suggestive of exaggerated incentive salience for drug-related cues, and when such ERPs are yet larger than ERPs elicited by naturally pleasant images, it may be possible to infer hedonic dysregulation and/or decreased responsiveness to natural rewards.

With regards to such ERPs, LPP amplitude may be an ideal candidate for detecting cue-induced reactivity over time in individuals or at a group level. It has been found to reliably track motivational salience and attentional responses to affective stimuli over repeated measurements. And, in individuals with drug addictions, it may track drug-related cue reactivity and provide insight into changes in motivational salience, sign-tracking, and the risks associated with them, such as the "incubated vulnerability" for lapse or relapse depicted in FIG. 2.

Various Aspects of Exemplary Systems

Figure 4:
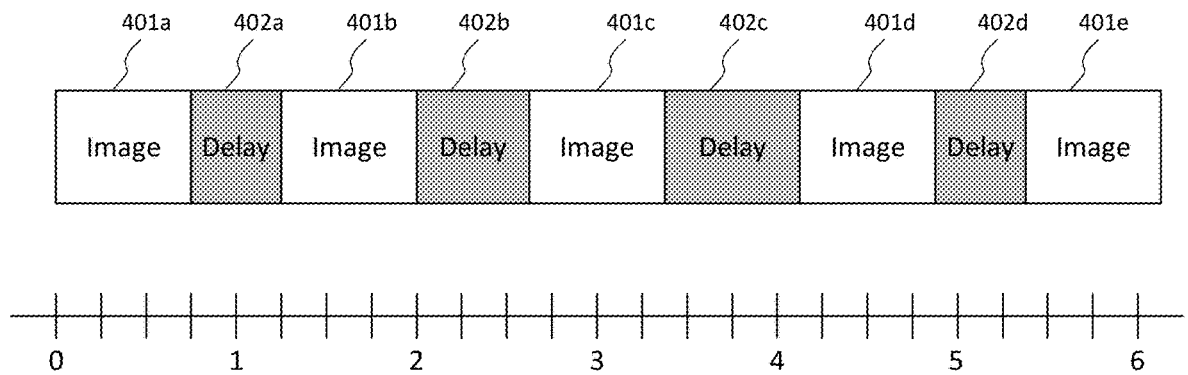
FIG. 4 illustrates an exemplary timeline of presenting stimuli.

FIG. 4 depicts a process by which ERP signals may be elicited and captured, in some implementations. An image 401a may be presented to a "user" (e.g., a patient, in some implementations, or other person whose cue reactivity is of clinical interest). In some implementations, the image 401a may be presented for 750 milliseconds; in other implementations the time may be shorter or longer. In general, a sequence of images 401a-401e may be presented in relatively rapid succession to elicit multiple ERP responses to multiple images and adequately measure ERPs to a range of content (e.g., affective cues of varying pleasantness and intensity, non-drug-vs. drug-related cues). A delay, such as the delay 402a may be provided between image 401a and the next image 401b. In some implementations, this delay may be 250 milliseconds or 500 milliseconds. In some implementations, random variation in latency between pictures within a specified range (e.g., +/−250 milliseconds) is included to reduce interference among ERPs elicited in close temporal order.

Figure 6A:
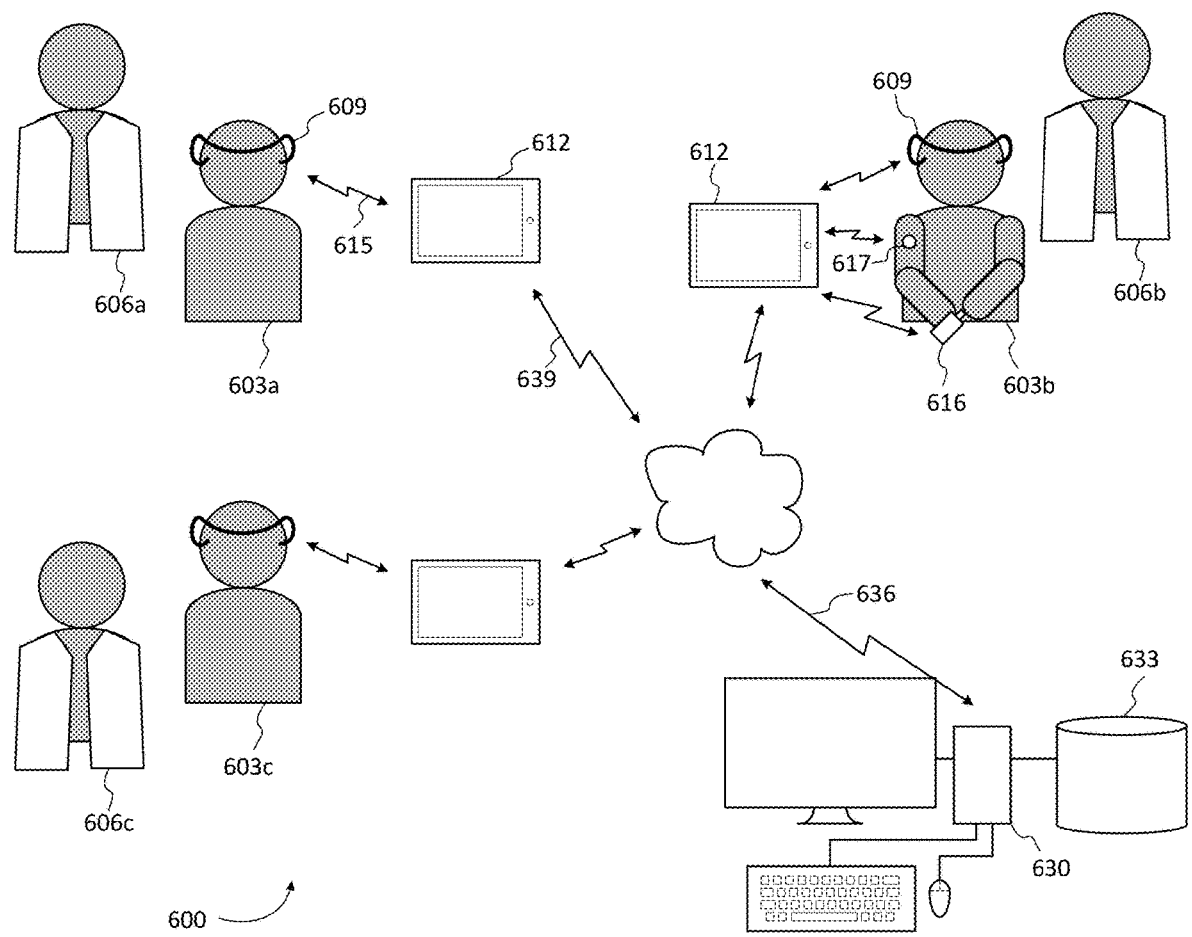
FIG. 6A is a diagram of an exemplary ecosystem for collecting and analyzing user data.

In some implementations, the user may provide a behavioral response (e.g., triggering an actuator, such as the actuator 616 shown in FIG. 6A) to the presentation of certain pictures, which actuation then may be registered (e.g., by the computing device 612 shown in FIG. 6A). As the sequence of images 401a-401e is presented, an EEG may be captured from the user viewing of the images (e.g., a patient undergoing therapy).

Figure 5:
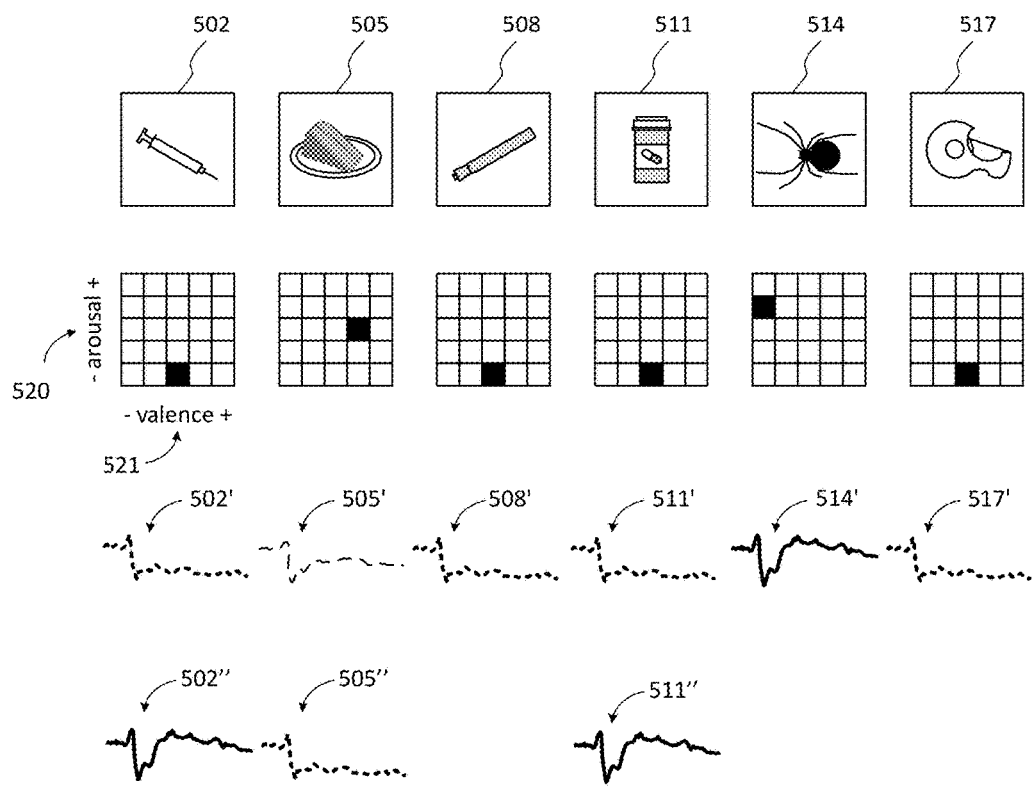
FIG. 5 illustrates additional detail associated with presentation of stimuli and capture of corresponding electroencephalographic (EEG) signals.

FIG. 5 illustrates features of images that may be used to elicit ERP signals. For example, the images may be characterized by features reflecting the semantic content of the images. Here, with reference to opioid drugs such as prescription pain killers or heroin, images might be categorized into a "drug-related" category containing a hypodermic needle/syringe (image 502) or pill bottle (image 511), and a "non-drug-related" category containing chocolate cake (image 505), highlighter pen (image 508), venomous spider (image 514), or tape dispenser (image 517). Categories may be flexibly used to isolate different semantic content in the images and target different forms of motivational salience and attention bias, e.g., images of cigarettes, ashtrays, etc. are considered "drug-related" for chronically addicted cigarette smoking populations; images of fast-food advertisements, junk food, etc. may be considered "drug-related" for overeating populations, etc. Additionally, coarse- (e.g., "fast-food") or fine-grained (e.g., "cheeseburger," "soft-drink," "French fries," etc.) semantic content, in nominal or numerical representations, may be extracted from images using human or computer vision to identify certain content, and used for targeted applications (e.g., drug addiction, smoking, obesity, etc.) and populations (e.g., treatment seeking drug users, smokers, overweight people, etc.).

Each image may be accompanied by one or more numerical or ordinal variables which describe the affective content in the image, such as affective intensity (520, capturing how intense an emotion the image typically elicits) and affective valence/pleasantness (521, capturing how pleasant or unpleasant an emotion the image typically elicits). In some implementations, such affective variables reflect the typical affective intensity or valence ratings, often derived as the average value from survey data from a large normative sample of people.

As shown, for example, the typical rating may be represented by darkened squares in the grids corresponding to the images. Thus, the images 502 (syringe), 508 (highlighter), 511 (pill bottle) and 517 (tape dispenser) are shown to have neutral valence based on their typical pleasantness ratings. By comparison, image 505 (cake) is associated with a typical moderate pleasantness rating, with moderate affective intensity; image 514 (spider) is associated with a typical very unpleasant rating, with relatively high affective intensity. In some implementations, other ordinal or numerical variables may be similarly used to represent other attributes of images (e.g., physical properties such as color hue, saturation, or brightness).

Expected ERP signals for each electrode corresponding to each image may be derived. As shown in this implementation, ERP signals 502', 508', 511' and 517' are expected have small amplitude LPP peaks, based on their typical low affective intensity. ERP signal 505' may be expected to a have a larger amplitude LPP peak, given the associated higher affective intensity. And ERP signal 514' may be expected to have an even larger amplitude LPP peak, given its even higher affective intensity.

By contrasting a user's ERP signals relative to expected ERPs based on variables reflecting the semantic (e.g., drug vs. non-drug) and affective (e.g., pleasantness/valence, affective intensity) content of images, it may be possible to quantify cue reactivity and sign-tracking for that person, which may be useful for inferring incentive or motivational salience of addiction-related cues, thus enabling clinical insights into risks associated with addiction, such as lapse or relapse. For example, if signals elicited by the syringe in image 502 or the pill bottle in image 511 were 502" and 511", rather than the expected 502' and 511', it may be inferred that the person exhibits a draw towards those stimuli. In the context of opioid addiction, where a syringe or pill bottle may be frequently associated with the taking or procurement of opioid drugs, this pattern of ERPs may suggest substantial conditioned cue reactivity, and possibly sign-tracking. Or, if an ERP elicited by a pleasant image, such as image 505 of cake, is smaller than expected (e.g., 505" instead of 505'), an inference may, in some cases, suggest that the person's motivational salience attributed to naturally pleasant images is diminished, perhaps reflecting the brain's reward system being downregulated by psychological disorder. For example, in the case of a drug addiction, a smaller-than-expected response may be indicative of normal hedonic reactions to natural rewarding stimuli still being dulled by brain circuits having been affected by the prior exposure to drugs.

FIG. 6A is a diagram of an ecosystem 600 for collecting and analyzing user data. Within the ecosystem 600 are users 603a, 603b and 603c, each of whom is under the professional observation of corresponding trained personnel (e.g., a clinician, technician, scientist, etc.) 606a, 606b and 606c, who in some implementation is in the same room as the user, or in other implementations may monitor the process remotely. As shown, user 603a is fitted with a portable EEG headset 609, which is coupled to tablet computing device ("tablet") 612 via a wireless connection 615 (e.g., Bluetooth, WiFi, etc.).

In some implementations, additional devices may be wirelessly linked to the computing device 612. For example, a user 603b may be provided with an actuator 616 (e.g., a pushbutton switch that is wirelessly connected to the computing device 612) to be actuated at a specific time, or when the user 603b becomes consciously aware of a physiological reaction or of a particular image. As another example, a sensor 617 (e.g., a skin conductivity, heart rate, temperature, blood pressure, respiration, etc.) may be wirelessly coupled to the computing device 612 to, for example, record physiological reactions of the user 603b to inputs received from the computing device 612 or other sources.

In some implementations, the tablet 612 provides a graphical user interface for interacting with the user 603a. In particular, the tablet 612 may be used to collect data from the user 603a, such as ongoing treatment details (e.g., in the case of drug addiction treatment, symptoms or other details of the past addiction; phase of treatment; recovery or abstinence data; subjective assessment of cravings; etc.). In addition, the tablet 612 may display to the user a sequence of images, such as the sequences depicted in and described with reference to FIG. 4 and FIG. 5.

As a sequence of images are being displayed on the tablet 612, EEG data can be captured from the user 603a, by the portable EEG headset 609; and this data can be transmitted to the tablet 612 via the interface 615, in a manner that is time-synchronized with each displayed image. In some implementations, data from both devices 609 and 612 may be sent to another computing unit (e.g., device 630). For example, with reference to FIG. 5, EEG data 508' may be captured and linked to image 508; EEG data 514' may be captured and associated with image 514; and so on.

Some amount of processing of the EEG data may be performed on the headset 609 or tablet 612 (depending on the processing capabilities of the devices). For example, in some implementations, raw EEG signals may be filtered to remove noise (e.g., artifacts associated with eye or user movements, muscle tension, electrical interference, etc.). In some implementations, additional filtering and signal processing is performed—for example, measurements may be extracted using one or more "data reduction" techniques, such as calculating the average value within one or more latency period (e.g., LPP average voltage within period 307), general linear modeling, blind source separation (e.g., principal or independent component analysis), etc.

Additional processing may be performed on the reduced, extracted data to, for example, identify indications of cue reactivity and sign-tracking. In some implementations, this additional processing may include computational modeling (e.g., linear regression or other statistical procedures) of the EEG as it relates to semantic content or affective dimensions. For example, with reference to FIG. 5, extracted data from ERPs elicited by image 508 (a highlighter) and image 517 (tape dispenser) may be grouped into either "non-drug" or "neutral pleasantness" categories, as they meet criteria for both of these conditions. Depending on the analysis of interest for a given user, say a person with opioid drug addiction, extracted data from ERPs elicited by image 502 (syringe) and image 511 (pill bottle) may be grouped into a "drug-related" category.

Extracted and processed EEG data may be further summarized for a specific user using repeated-measures statistical analyses. For example, in some implementations, processed ERP data from one category is compared to processed ERP data from another category from the same user; such within-person comparisons may be performed within session, or, processed ERP data from one category in one session (e.g., a given stage of treatment) is compared to processed ERP from the same category in another session (e.g., a different stage of treatment), etc. As described with reference to FIG. 5, at an early point in treatment, a larger response to images 502 (syringe) and image 511 (pill bottle) than to image 508 (highlighter) and image 517 (tape dispenser) may indicate exaggerated cue reactivity to opioid drug-related cues. However, at a later point in treatment, a smaller response to image 502 (syringe) and image 511 (pill bottle) than was identified in the same person at an earlier point in treatment may provide objective evidence of normalization of cue reactivity and progress of treatment for that person.

In some implementations, additional repeated-measures statistical analyses may be performed to compare ERPs elicited by "drug-related" cues (which are typically of low affective intensity), to ERPs elicited by high affective intensity "non-drug-related" cues. For example, rather than comparing image 502 (syringe) and image 511 (pill bottle) to neutral images (e.g., image 508 (highlighter) and image 517 (tape dispenser), the comparison may be made to affectively intense images (e.g., image 505 (cake) and image 514 (spider)). In some users, such comparisons between drug-related cues and affective cues may provide a better indication of cue reactivity, and sign-tracking in particular. In other implementations, comparisons may be made to population-level data (e.g., data collected from a large sample of users), through, for example, interface to other elements of the ecosystem 600 which are now described.

The ecosystem 600 can include a centralized computing facility 630 (e.g., a processor, data store 633 and network interface facilities 636 and 639). The centralized computing facility 630 may receive data (e.g., EEG/ERP data, clinical data, recovery and treatment variables, etc.) and store it in the data store 633. The interfaces 639 and 636 may represent broadband connections to a remote, cloud-based processing unit 630 or processing units.

In some implementations, the processor 630 and data store 633 may contain population-level data and inform user-level (e.g., expected ERPs and statistics for comparable images—for people with similar or different clinical features, demographics (age, gender, etc.), treatment details, etc.) back to individual tablets (e.g., tablet 612), for use as a comparison in individual clinical applications and settings (e.g., clinician 606a and user 603a).

As described above, device 612 was referred to as a tablet computing device. Other types of computing devices may be possible, such as portable, notebook or laptop computers; smart televisions; watches; smart phones; and other electronic devices having computing functionality, a graphical user interface, and wireless communication facilities.

Figure 6B:
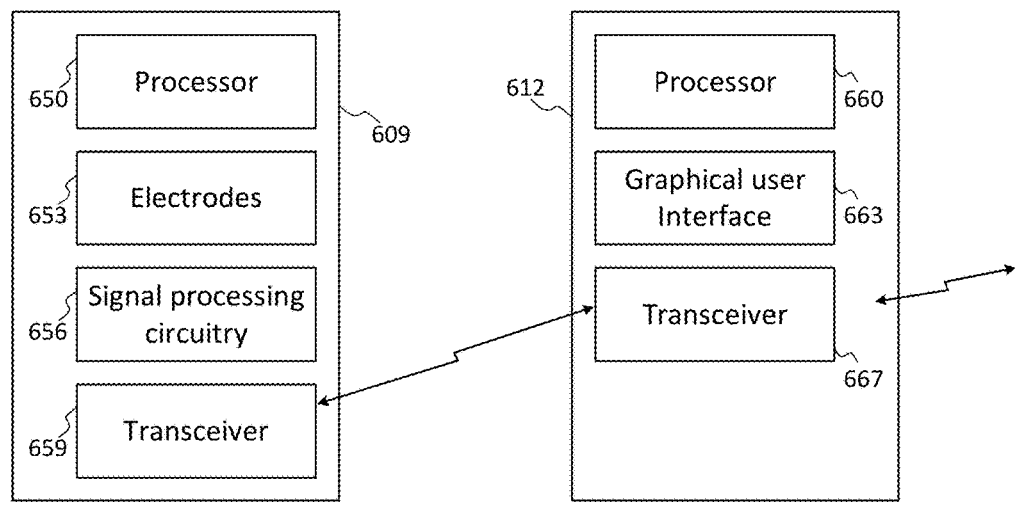
FIG. 6B illustrates additional exemplary detail of two components of the exemplary ecosystem of FIG. 6A.

FIG. 6B illustrates exemplary components of the portable EEG headset 609 and the computing device 612. As shown, the portable EEG headset 609 includes a processor 650, electrodes 653 that are configured to interface to the skin and/or scalp of a user, signal processing circuitry 656 that is configured to process electrical signals from the electrodes (e.g., electrical neural signals from a user wearing the portable headset 609; processing may include, for example, amplifying and filtering noise from the electrical neural signals), and a transceiver 659 (e.g., a Bluetooth, Wi-Fi, infrared or other near-field communication transceiver for exchanging information with another device, such as the computing device 612). The portable EEG headset 609 may include other components and systems (not shown) that are customary for an electronics or computing device (a power source, memory, user interface elements, indicators, output devices etc.).

As shown, the computing device 612 also includes a processor 660, a graphical user interface 663 (e.g., for displaying images to a user of the computing device 612, such as the user 603b); and a transceiver 667 for exchanging information with the portable EEG headset 609 (e.g., through the transceiver 659 of the portable EEG headset 609) and for communicating with other external devices (e.g., a centralized computing facility 630). The computing device 612 may also include other components and systems (not shown) that are customary for computing devices (power source, memory, user interface elements, indicators, output devices etc.).

Figure 7:
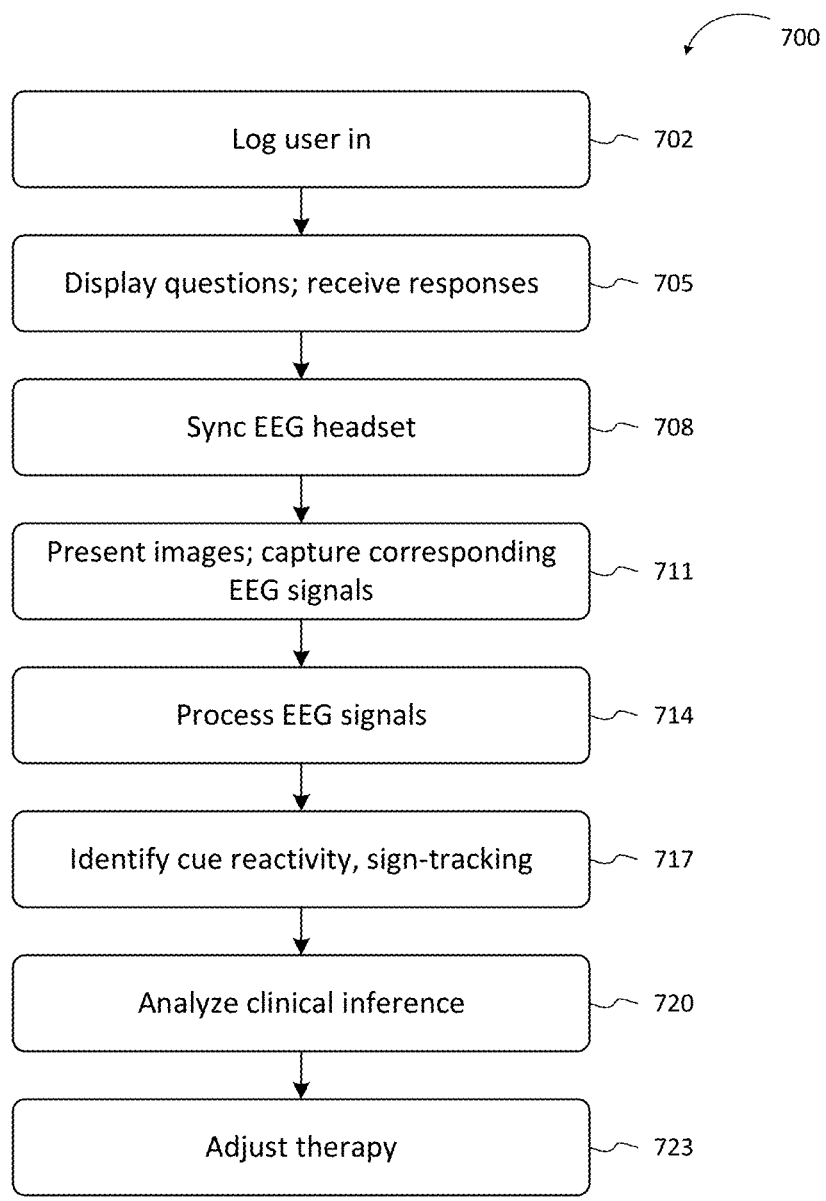
FIG. 7 is a flow diagram of an exemplary method that may be executed by a processor.

FIG. 7 is a flow diagram an exemplary method 700 that may be executed by one or more processors (e.g., the processor 650 (see FIG. 6B) in the portable EEG headset 609, or the processor 660 in the computing device 612, or by a combination of the processor 650 and processor 660 working in conjunction with each other). As shown, the method includes logging in (702) a user. For example, the clinician 606a may assist the user 603a in logging into an account that is specific to the user 603a. An electronic health record or record associated with therapy may be stored on the tablet 612 itself, or in the data store 633, or in both places.

The method 700 includes displaying (705) questions and receiving (705) responses. For example, questions may be displayed (705) to the user 603a on the graphical user interface of the tablet 612, and the same graphical user interface may be used to receive (705) responses. The questions and responses may relate to the user 603a, treatment progress for the user 603a, subjective feelings of craving by the user 603*a*, stage in therapy, medications that user 603*a* is taking, biographical data about the user 603*a*, etc.

The method 700 includes syncing (708) an EEG headset. For example, an EEG headset 609 worn by the user 603*a* may be powered on, and a connection 615 may be established between the headset 609 and the tablet 612 (e.g., a Bluetooth, WiFi or other wireless or wired connection). Syncing (708) the EEG headset may also include a quality assurance or self-test algorithm that confirms proper functioning of the headset 609 and proper function of electrodes on the headset.

The method 700 includes presenting (711) images and capturing (711) corresponding EEG signals For example, images, such as images 502, 505, 508, 511, 514 and 517 may be presented by the graphical user interface of the tablet, as depicted in FIG. 5, with inter-image delays as depicted in FIG. 4. Simultaneously, the EEG headset 609 may capture (711) EEG signals from the user 603*a* that are elicited by the display of the images. That is, the EEG signals may capture brain activity that is responsive to the user 603*a* viewing the images that were presented (711). In particular, EEG signals may be captured (711) such as signals 502' or 502" in response to presentation (711) of image 502; or signals 505' or 505" in response to presentation (711) of image 505.

The method 700 includes processing (714) the captured (711) EEG signals. For example, artifacts may be removed from the signals, such as noise associated with eye or user movements, muscle tension, electrical interference, etc. Processing (714) may further include identifying relevant portions of the EEG signals and associating them with specific images. For example, with reference to FIG. 3, portions of the EEG signals corresponding to time periods 304 and/or 307 may be extracted and associated with specific images.

The method 700 includes identifying (717) conditioned and unconditioned cue reactivity and sign-tracking. For example, the method 700 may identify (717) that EEG signal 502' was expected but that signal 502" was received (e.g., indicating a strong, affective response to drug-related stimulus). The identifying (717) may result from comparing an EEG signal to a threshold signal. For example, a received EEG signal for a drug-related stimulus may be compared to another EEG signal from the same user (or series of averaged EEG signals) from the same neutral or affective category Alternatively, an EEG signal for a drug-related stimulus may be compared to a population-level "expected" value—such as the average value obtained from a large sample of users, stored in the data store 633.

Optionally, the method 700 may include analyzing (720) user data relative to a larger population of other users or from other databases. This may include the comparisons described above for identifying (717) cue reactivity and sign-tracking; and this analyzing (720) may include additional analyses, such as statistical analyses based on, for example, age, gender, type of addiction, stage of addiction treatment, type of medication used during therapy, type of therapy, therapist, region of country, etc. In some implementations, data is transmitted and stored to the data store 633 for use in future population-level studies and comparisons.

Optionally, the method 700 may include adjusting (723) therapy. For example, when abnormal cue reactivity or drug-related sign-tracking is identified, medication may be added or altered, treatment time may be truncated or extended, type of treatment may be adjusted, or other steps maybe taken, e.g., to minimize the probability of future problems (e.g., lapse, relapse). In some implementations, adjusting (723) therapy may include providing information to the user—such as, for example, information (e.g., reports or graphs) about the user's cue reactivity or sign-tracking, or historical changes to the user's cue reactivity or sign-tracking, which may show progress on the part of the user. In this manner, the method 700 may provide an improved way of minimizing relapse risk, in an objective manner, by identifying sign-tracking that may otherwise go undetected by other methods of treatment, such as, for example, by self-reported subjective assessments of craving.

Figure 8A:
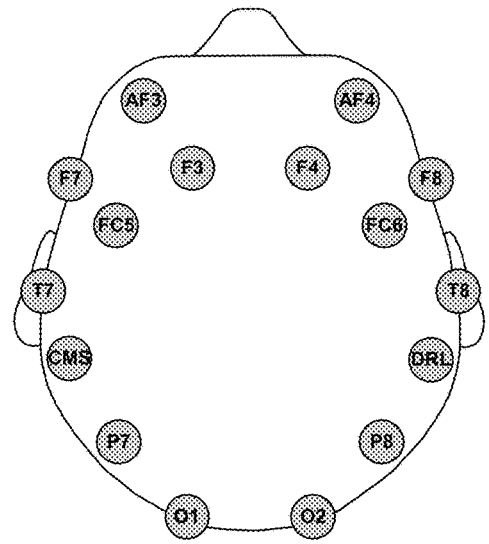
FIGS. 8A and 8B illustrate exemplary 16-channel and 64-channel EEG scalp locations for EEG monitoring devices.
Figure 8B:
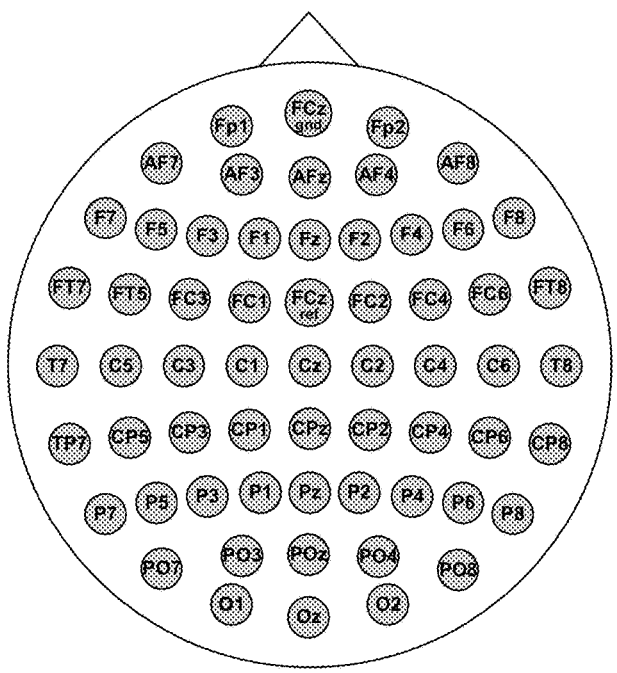

FIG. 8A illustrates exemplary 16-channel EEG scalp locations, and FIG. 8B illustrates exemplary 64-channel EEG locations that may be employed by various EEG monitoring devices, such as, for example, a headset 609 depicted in FIG. 6A. In some implementations, a subset of the standard EEG channel locations may be employed. For example, in some implementations, a headset (e.g., headset 609 in FIG. 6A) includes EEG channels CP6, F6, C4, CP4, CP3, C3, F5 and CP5. In some implementations, the headset 609 includes EEG channels AF3, F7, F3, FCS, T7, P7, O1, O2, P8, T8, FC6, F4, F8 and AF4.

In addition to characterizing standard EEG electrode locations, as shown in FIG. 8A and FIG. 8B, some electrodes may also be employed as one or more electrical grounding and/or referencing electrodes (e.g., to enable removing common mode noise). In FIG. 8B, for example, electrode "FCz gnd" and "FCz ref" may be used for subtracting "common mode" noise (e.g., electrical interference from wall power sources, etc.) and referencing signals to a "zero" point for the EEG acquisition system.

In some implementations, an EEG headset includes EEG channels that do not correspond with standard EEG channel leads but that are rather configured to capture, for example, signals related to human-computer interaction implementations, video gaming implementations, meditation or other wellness implementations, biomedical/clinical implementations, biofeedback or neurofeedback implementations, etc. Additionally, the nature of the EEG electrodes may come in various applications, such as "wet application" (e.g., requiring electroconductive saline or gel solutions), "dry application" (requiring no electroconductive solution), materials (e.g., Ag/AgCl, composite, etc.) and shapes (e.g., flat, cup, comb, polymer or other adhesive). In some implementations, it may not be critical which precise locations are measured by an EEG headset, provided that ERP signals having affect-modulated ERP features can be captured (e.g., as depicted in and described with reference to FIG. 3).

Figure 8C:
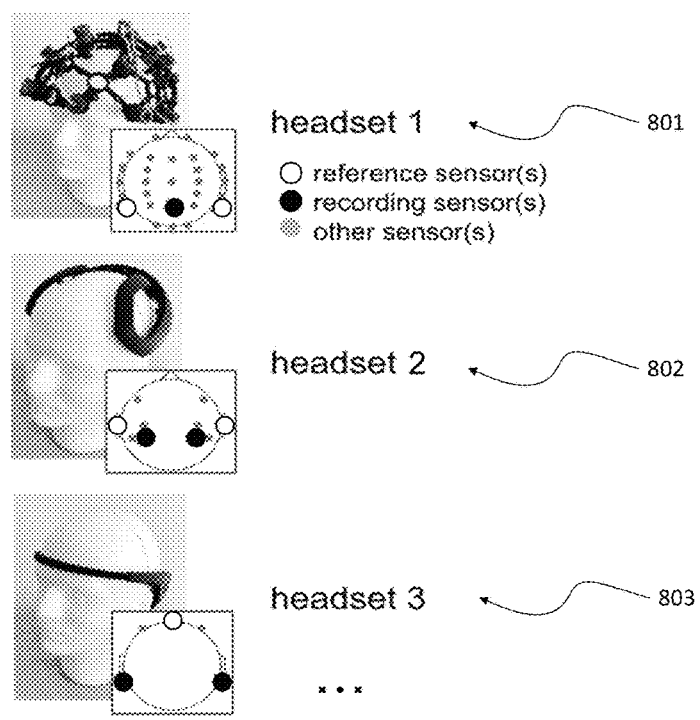
FIG. 8C illustrates exemplary EEG headsets.

FIG. 8C illustrates three exemplary EEG headsets—headset 801, headset 802, and headset 803. As shown, the EEG headsets may vary in the number and position of electrodes included, and this variation may facilitate use of the EEG headsets in different applications. For example, the headset 801 may be a high-resolution, high-electrode count EEG headset suitable for in-laboratory research applications. As another example, headset 802 and headset 803 may be configured for recreational, personal, or commercial users and may have fewer electrodes than headset 801. By way of example, an EEG headset could be the "Notion" or "Crown" device made by Neurosity Inc. (Brooklyn, NY); the "Muse" device made by InterAxon (Los Angeles, CA); or another similar commercially available portable EEG device.

Regardless of the specific form factor, exemplary EEG headsets such as the headsets 801, 802 and 803, include a plurality of electrodes for sensing electrical signals of a user that correspond to brain activity of the user. In addition to the electrodes, an exemplary EEG headset typically includes processing equipment for converting received signals into digital information. For example, as described with reference to FIG. 6B, an exemplary EEG headset may include a microprocessor, power supply (e.g., rechargeable battery), memory and various interfaces for coupling the electrodes to the microprocessor and for coupling microprocessor output to an external device (see generally, FIG. 6B). More particularly, interfaces may include signal processing electronics for isolating electrical neural signals of a user from other ambient electrical noise (e.g., the signal processing electronics may include various amplification and filtering circuitry), and other circuitry for digitizing analog signals from the electrodes for digital processing by the microprocessor. Interfaces may further include transceiver(s) for coupling an EEG headset to external devices (e.g., a computing device, such as the computing device 612 shown in FIG. 6A). In some implementations, such interfaces may include wireless networking capabilities (e.g., Bluetooth or Wi-Fi connections).

In some implementations, computing resources on an EEG headset may provide pre-processing of EEG signals before transmitting processed information to an external device. For example, a processor and memory on an EEG headset may execute programs (e.g., software or firmware stored in memory of the EEG headset and executed by a processor) to characterize or otherwise process measured EEG signals.

In some implementations, this characterization or processing may include determining arousal or valence measurements associated with specific images presented to a user of the EEG headset. For example, with reference to FIG. 5, FIG. 6A and FIG. 8C, a user 603b may be presented, via computing device 612, an image—such as the image 505 of a piece of chocolate cake, an image 514 of a venomous spider, or an image 517 of a tape dispenser. Timing of the presentation of the image 505, 514 or 517 may be synchronized with an EEG headset 609, such that electrical signals can be captured from the user, temporally relative to the point of image presentation. The headset 609 may then record a signal 505' or 505'', 515' or 517'; and electronics and processing functionality (e.g., a microprocessor running software or firmware in memory (not shown)) may determine corresponding values for valence 521 and arousal 520 associated with the presented image. These determined values may be transmitted back to the computing device 612 for further processing by that computing device 612 or by another computing device (e.g., the network-connected computing device 630).

Figure 8D:
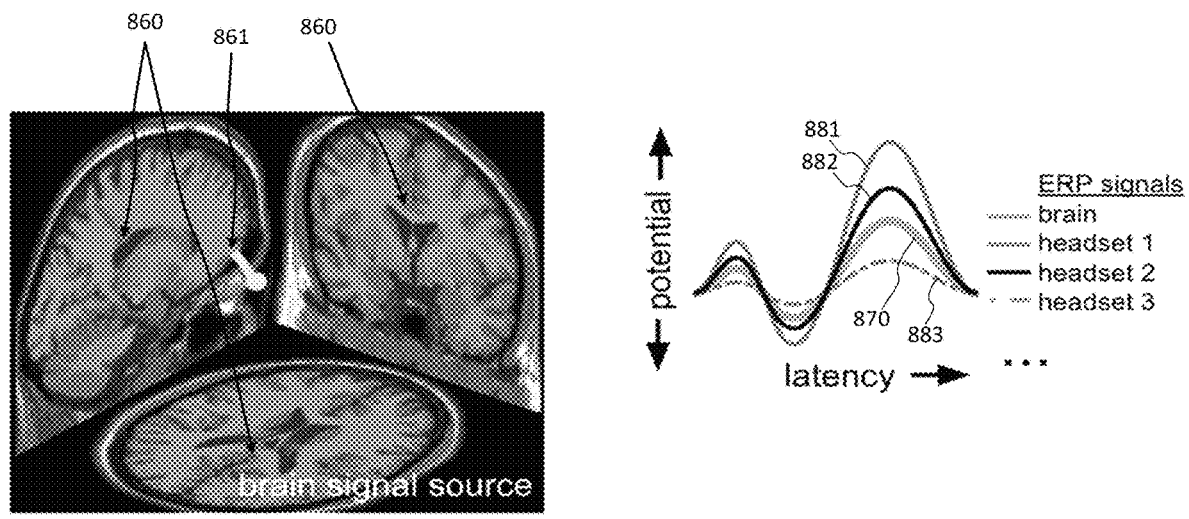
FIG. 8D depicts a region of a user's brain that may generate an electrical signal, and stylized waveforms of that signal as it may be picked up by various exemplary EEG headsets.

FIG. 8D depicts a location 860 within a user's brain (as viewed on three orthogonal anatomical planes) that may generate an electrical signal that can be measured from an EEG headset (e.g., in response to a stimulus or otherwise). To pick up such an electrical signal, a reference point 861 may be employed (e.g., a ground or reference electrode may be employed in such a way as to detect a signal associated with the reference point 861, for use in processing a signal associated with location 860). A corresponding actual electrical signal corresponding to the location 860 (relative to the reference location 861, in some implementations) is depicted in exemplary form as signal 870. Stylized versions of corresponding signals that may be measured by various EEG headsets are also displayed. For example, in some implementations, signal 881 may be representative of a signal that the headset 801 may detect; signal 882 may be representative of a signal that the headset 802 may detect; and signal 883 may be representative of a signal that the headset 803 may detect. While stylized as shown, these signals 881, 882 and 883 may take a form like that shown in and described with reference to FIG. 3, for example, in response to a particular stimulus.

Figure 9A:
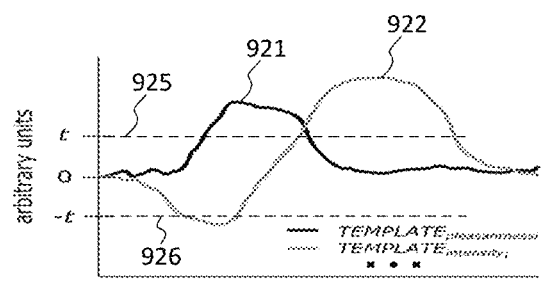
FIG. 9A depicts exemplary templates that may be employed to characterize EEG/ERP signals.

FIGS. 9A-9D depict on exemplary way affective pleasantness and intensity values may be characterized. In some implementations, such values may correspond to "arousal" and "valence" described with reference to FIG. 5. As depicted in FIG. 9A, a template 921 for pleasantness and a template 922 for intensity may be defined. In some implementations, templates 921 or 922 are defined for specific semantic categories of images (e.g., drug-related, non-drug-related, predicted to elicit a strongly negative response, predicted to elicit a strongly positive response, predicted to elicit a neutral response, etc.). In some implementations, templates are defined from expected values for particular EEG signals, from a normative population, at a particular electrode of an EEG headset (denoted by the i subscript). For example, the templates 921 and 922 shown in FIG. 9A may be correspond to expected ERP values for pleasantness and intensity associated with presentation of an image that a normative sample of a population may consider to be negative, with moderate intensity. In some implementations, different sets of templates may be defined for different images and for different electrodes associated with a given EEG headset. In some implementations, additional or alternate templates may be used for different dimensions of data (e.g., physical properties of the image, such as color hue, value, saturation, etc.).

As shown in FIG. 9A, the y-axis units may be arbitrary, in some implementations. For example, the units may map to a range that spans expected minimum and maximum readings for an electrical signal that is picked up from an EEG headset. The x-axis may correspond to a time axis, with t=0 corresponding, in some implementations, to presentation of a stimulus (e.g., an image) to a user of the EEG headset.

Thresholds (e.g., an upper threshold 925 and a lower threshold 926) may be defined. In some implementations, such an upper threshold 925 and lower threshold 926 may correspond to a level at which a received signal would be considered to be beyond the expected value for a normative population. For example, a value associated with an EEG from a particular user that is above the threshold 925 for pleasantness may indicate an association with a stimulus that is more attractive to that particular user than would be expected of the normative population; similarly, a value associated with an EEG from a particular user that is below the threshold 926 for intensity may indicate a stronger negative reaction to the corresponding stimulus than would be expected of the normative population.

By analyzing EEG signals associated with a particular user, in response to particular stimuli, cue reactivity of that particular user may be determined, in some implementations. And in such implementations, clinically relevant information may be obtained that can be employed to improve treatment. For example, if a clinician is working with a user who has a history of opioid addiction, the clinician may examine EEG readings relative to the templates described above to infer cue reactivity (and, in some implementations, susceptibility to relapse). In particular, the clinician may present the user with an image of a pill bottle (e.g., image 511, from FIG. 5) and examine subsequent EEG signals relative to templates for a given electrode and a normative population. EEG signals that—when analyzed relative to appropriate templates—indicate a high degree of pleasantness and intensity may suggest that the user is prone to relapse. Such information, in the hands of a clinician, may enable the clinician to adjust therapy that may be provided to the user, in order to, for example, improve the effectiveness of the treatment or minimize the chance of a future relapse.

Figure 9B:
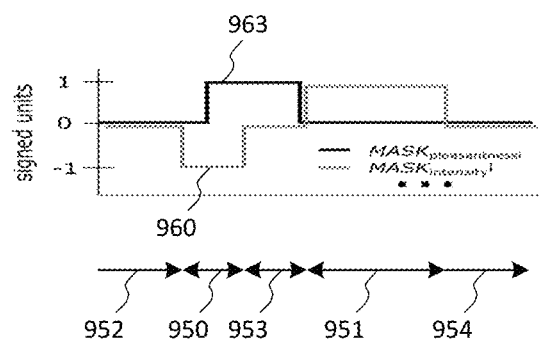
FIG. 9B depicts exemplary digitized mask versions of the templates shown in FIG. 9A.

FIG. 9B depicts a way the templates 921 and 922 may be "digitized" to facilitate their application to other signals (e.g., ERP signals). As shown in FIG. 9B, the templates 921 and 922 may be translated to regions (i) in which the template values are within the bounds of the upper threshold 925 and the lower threshold 926 and (ii) in which the template values are above the upper threshold 925 or below the lower threshold 926. These regions may have a sign (positive or negative) but otherwise have no units (other than 0, −1 or +1). Thus, as shown, a region 950 may correspond to when signal 922 is lower than threshold 926. Since the signal is lower than the lower threshold 926, the region may be assigned a negative unitary value. A region 951 may correspond to the same signal 922 exceeding the upper threshold 925 and thus be assigned a positive unitary value. When the signal 922 is between the upper threshold 925 and lower threshold 926, a corresponding digital mask 960 may have a zero value, in region 952, 953 and 954. The above description applies to the intensity template 922; but similar regions can be assigned to the pleasantness signal 921. Thus, a digital mask 960 may be generated to correspond to the intensity template 922 and its corresponding upper threshold 925 and lower threshold 926; and a digital mask 963 may be generated to correspond to the pleasantness template 921 and its corresponding upper threshold 925 and lower threshold 926.

In some implementations, the digital masks 960 and 963 may be represented by a discrete series of values (e.g., −1, 0 and +1), spaced at a fixed time interval (e.g., an interval associated with a sampling rate that may be used in analog-to-digital conversion of underlying EEG or ERP signals). When the masks are so represented, digital signal analysis of the underlying EEG or ERP may be facilitated—for example, through a digital convolution or dot product of the underlying EEG or ERP signal and the corresponding template.

In the above description, a normative population is referenced, but this could also be prior historical data from the user. Such prior historical data could be used to assess change, progress, relapse, etc. from a given user going through therapy.

Figure 9C:
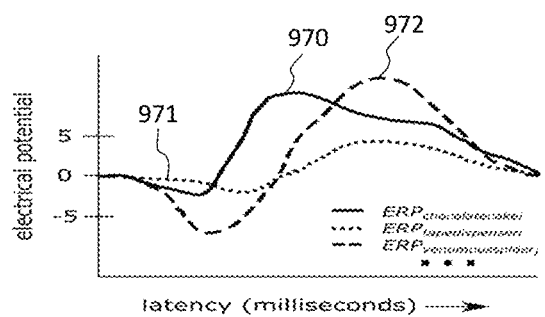
FIG. 9C depicts stylized, exemplary ERP signals that may correspond to presentation of stimuli to a user.

FIG. 9C depicts stylized, exemplary ERP signals that correspond to presentation of particular stimuli (in the scenario depicted, particular images) to a user. That is, as depicted, a user wearing an EEG headset (e.g., the headset 802 of FIG. 8C), when presented with an image 505 of chocolate cake, has a physiological response that results in signal 970 being captured by the EEG headset (as used herein, "captured" includes acquisition of a raw electrical signal, in a time-synchronized manner relative to the stimulus; its filtering by corresponding electronics to isolate the signal from noise; and its processing for presentation as an ERP signal). Similarly, when the same user wearing the same EEG headset is presented with an image 517 of a tape dispenser has a physiological response that results in signal 971 being captured by the EEG headset. Similarly, when the same user wearing the same EEG headset is presented with an image 514 of a venomous spider has a physiological response that results in signal 972 being captured by the EEG headset.

Figure 9D:
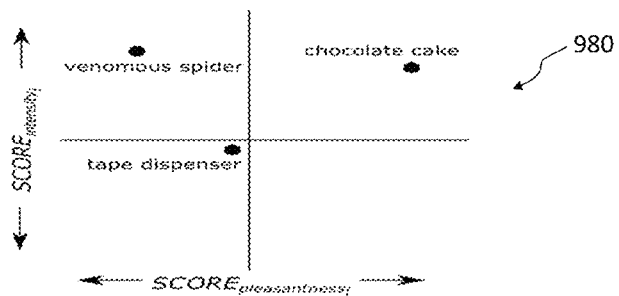
FIG. 9D illustrates an exemplary two-dimensional mapping that may be employed to display aspects to a user's response to stimuli.

In some implementations, ERP signals—such as the ERP signals 970, 971 and 972 from FIG. 9C—can be processed using the digital masks 960 and 963 to map a user's physiological response (e.g., EEG/ERP signals) to specific images in an intensity/pleasantness space—such as the two-dimensional space 980 depicted in FIG. 9D. As depicted, response can, in some implementations, be mapped based on intensity and pleasantness. In some implementations, as depicted, the mapping may be specific to a particular electrode (e.g., as denoted by the i subscript). Mapping to (in the case shown, a two-dimensional) space, can facilitate visual comparisons between different images (and their corresponding physiological effect), the same images presented to different users, the same images presented to the same user over a period of time, etc. With such a mapping, it may be possible for a clinician to track progress (e.g., of therapy related to certain images that are presented) for a particular user, or to identify proclivities or subconscious elements of cue reactivity that may, in some cases, be useful in predicting relapse or progress of therapies or treatments.

FIGS. 9A-9D are merely exemplary. Numerous variations are possible. For example, the two-dimensional space that is illustrated in FIG. 9D may be, in some implementations, a three-dimensional or n-dimensional space. Masks are described with respect to discrete-time convolution or dot product operations, but the same results of identifying values that are outside of an expected range at particular time periods relative to a stimulus event may be employed. Factors other than or in addition to affective intensity/arousal or pleasantness/valence may be explored and mapped. Template or threshold data that is "normative" may be drawn from various sources, including, for example, a general population or a smaller population having commonalities (e.g., age, gender, past addiction types and substances, past addiction lengths, past therapies applied, etc.). Templates and masks may be derived from individuals (e.g., within a given EEG session), or they may be derived from expected or population-level ERP signals. Importantly, the use of distinct templates or masks at each EEG channel i and location may enable a generalizable method for deriving scores from different EEG headset configurations (e.g., headsets 801, 802 or 803, shown in FIG. 8C).

Figure 10:
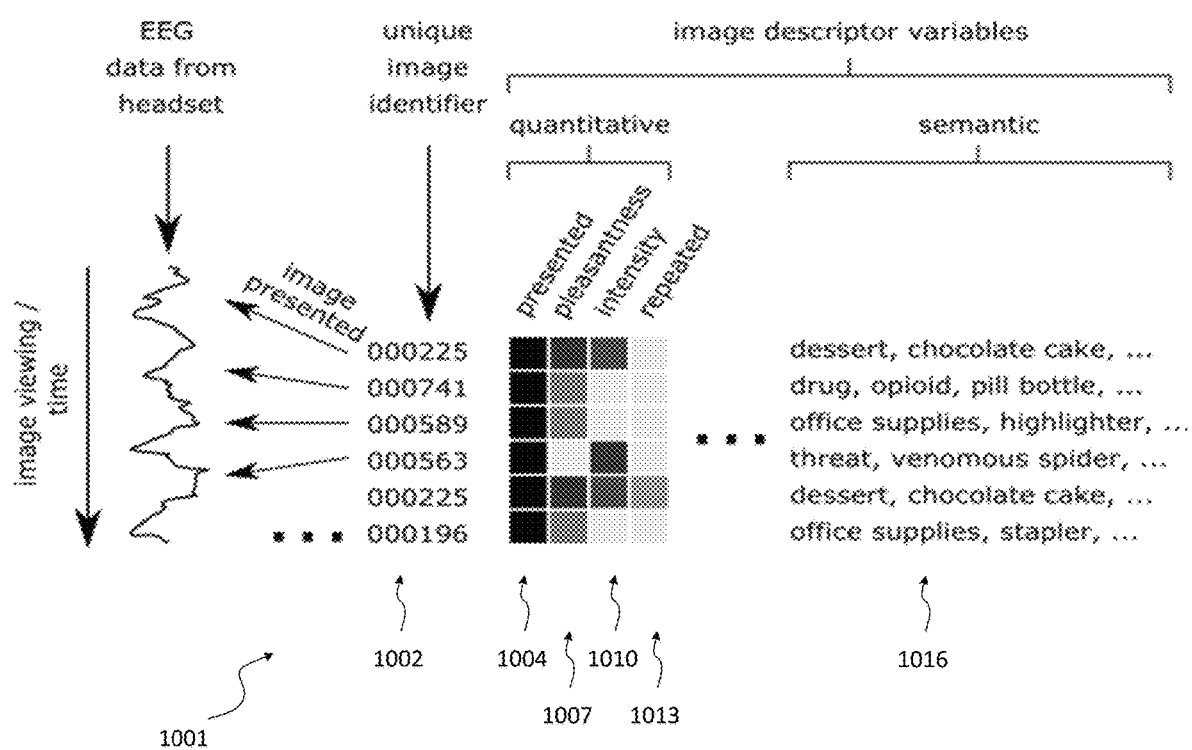
FIG. 10 depicts exemplary EEG data and meta data that may captured and stored in association with stimuli presented to a user.

FIG. 10 depicts exemplary EEG and meta data 1001 captured (e.g., captured (711) by the headset 609) in relationship to images displayed (e.g., images 502, 505, 508, etc., displayed on a graphical user interface of the tablet 612, to the user 603a). As shown, the data stored may include an identifier 1002 associated with specific images and various metadata about the images and/or a physiological reaction of a user to the specific images. For example, the metadata may include an indication 1004 of whether a specific image has been presented, a pleasantness value 1007 (e.g., in some implementations, an aggregate pleasantness value determined or calculated from one or more individual pleasantness values associated with one or more electrodes), an intensity value 1010 (e.g., an aggregate intensity value determined or calculated from one or more individual intensity values associated with one or more electrodes). In the implementation shown, the data may further include an indication 1013 of whether an image has been displayed multiple times (and, if so, an indication, in some implementations, of how many times). The data may also include semantic information 1016 about the image, which, in some implementations, may be used to categorize and analyze physiological responses to the image.

In some implementations, the data 1001 may be stored in a data store, such as the data store 633 shown in FIG. 6A, or in memory of a device such as the computing device 612. In some implementations, the data 1001 is stored in a table form, as depicted; in other implementations, the data 1001 may be stored in a relational database or other form of database in which data can be readily stored, retrieved and linked or associated with other data.

Figure 11:
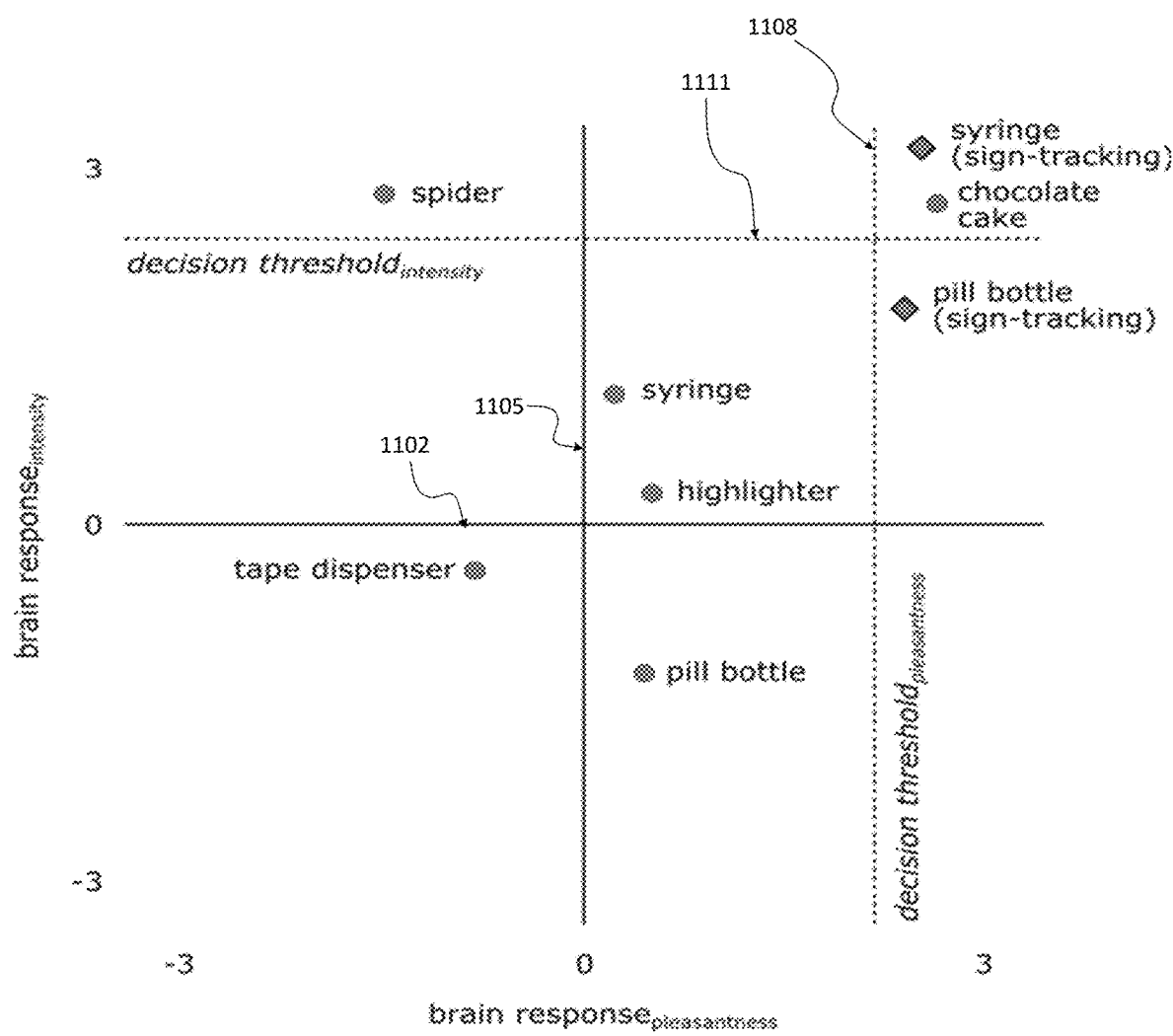
FIG. 11 depicts an exemplary view of data that may be mapped along multiple axes.

FIG. 11 depicts another view of data (e.g., neural or physiological responses to stimuli, such as images presented to a user) that may be mapped along a pleasantness axis 1102 and intensity axis 1105. Thresholds may be applied to the mapping—such as, for example, a threshold 1108 for pleasantness and a threshold 1111 for intensity. The thresholds may be configured such that values above these thresholds indicate or suggest sign-tracking or a high degree of cue reactivity.

With reference to FIG. 5 and FIG. 11, "pleasantness" may correspond to the valence spectrum 521; and "intensity" may correspond to the arousal spectrum 520. Values that are categorized in the upper right quadrant as shown in FIG. 11 may correspond to signals that are greater than an expected minimum threshold value. For example, with reference to FIG. 3, a signal 316 that is greater (e.g., on average, within a particular window, such as window 335) than signal 313, by, for example, a delta 340 (or greater than signal 310 by a delta 341) and may be classified in the upper quadrant of FIG. 11. When responses to drug-related cues appear in this quadrant, it may be an indication of cue reactivity, which can, as described herein, indicate potential sign-tracking and vulnerability to relapse.

Of values for which sign-tracking is suggested, a determination may be made as to the likelihood that sign-tracking is actually present based on an expected response of a normative population. For example, as depicted in FIG. 11, a normative population may be expected to, on average, have a reaction to an image of chocolate cake that is highly pleasant and highly intense; that same normative population may not be expected to have a similarly highly pleasant and intense reaction to an image of a syringe or pill bottle. Thus, a user of an EEG headset whose reaction to a syringe or pill bottle is as depicted in FIG. 11 may be flagged as likely exhibiting sign-tracking. A clinician may employ this information to modify therapy of the user (e.g., increase an anti-addiction medication, increase frequency or intensity of therapy, present information to the user to spur greater focus and commitment to therapy, etc.).

Figure 12:
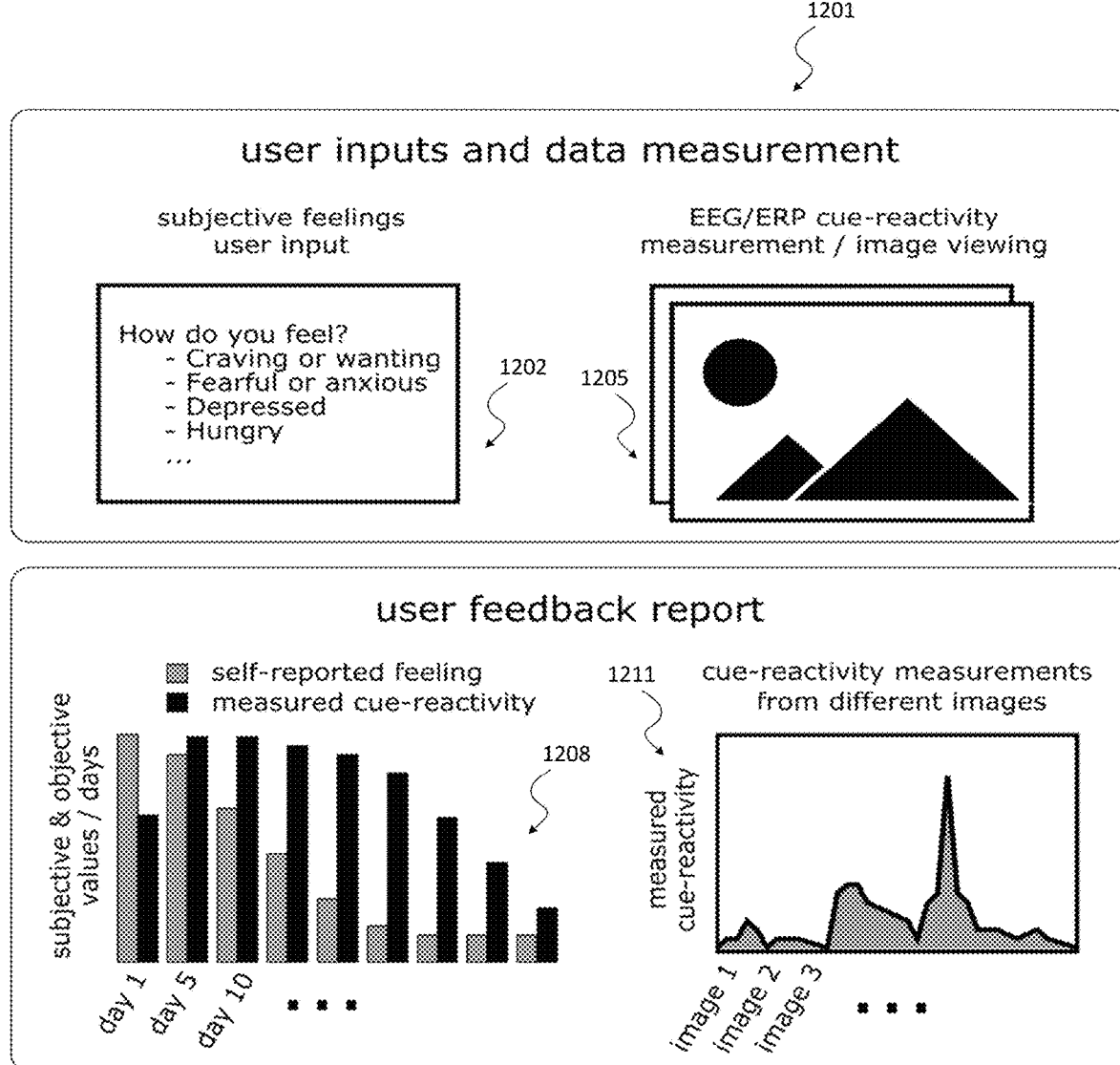
FIG. 12 illustrates aspects of an exemplary graphical interface.

FIG. 12 illustrates aspects of an exemplary graphical interface 1201 (e.g., screens that may be displayed (705) on the tablet 612 to receive (705) responses to displayed (705) questions). The graphical user interface 1201 may include an area 1202 for receiving subjective user input, such as subjective feelings of the user. The graphical user interface may include an area 1205 for displaying images and/or providing EEG/ERP cue-reactivity data. The graphical user interface 1201 may also provide various charts, graphs and reports—such as, for example, a chart 1208 comparing subjective, self-reported feelings of a user relative to more objectively measured cue-reactivity, and a graph 1211 illustrating cue-reactivity relative to specific images.

The foregoing and illustrated are merely exemplary. Numerous reports, charts, graphs and other means for presenting data are possible, to, for example, assist a clinician in providing therapy to a user, or in presenting the user with information that may be helpful. In some implementations, the various possible reports, graphs and charts may be generated in response to a method 700 that identifies (717) sign-tracking, analyzes (720) data relative to a population, or causes therapy to be adjusted (723). Various reports may be generated, for example for either user 603a or clinician 606a; or for other clinicians 606b or 606c in their delivery of therapy to other users 603b or 603c; or for storage in the data store 633 for further analysis.

Figure 13:
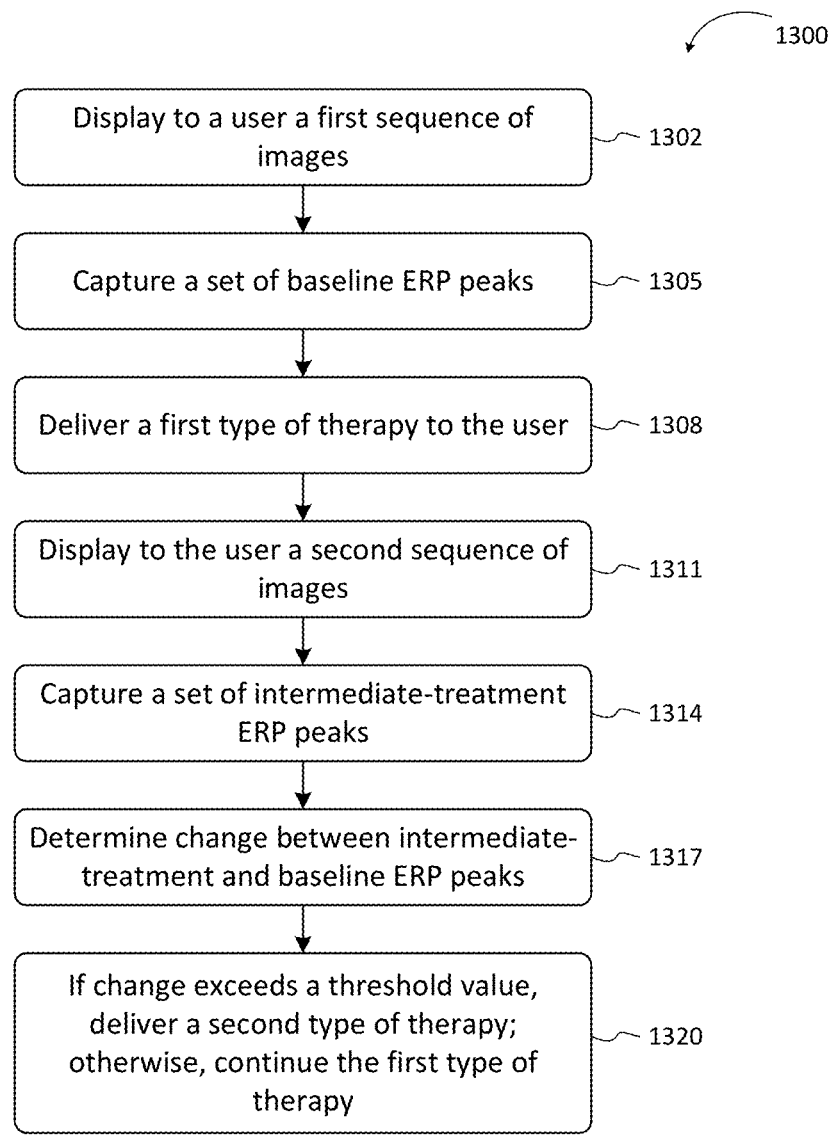
FIG. 13 is a flow diagram of an exemplary method of treating a person for an addictive or motivational salience disorder.

FIG. 13 illustrates an exemplary method 1300 of treating a person for an addictive or motivational salience disorder. As described here, the person being treated is a user of a portable EEG headset, such as the headset 609 shown in and described with reference to FIG. 6A.

The method 1300 includes displaying (1302) to the user a first sequence of images. For example, a sequence of images, such as the images 502, 505, 508, 511, 514 or 517 shown in FIG. 5 may be displayed to a user of a portable EEG headset (e.g., by being displaying on a portable computing device 612).

The method 1300 includes capturing (1305) from the user, with a portable EEG headset and in a time-synchronized manner relative to displaying the first sequence of images, a set of baseline ERP peaks associated with the first sequence of images. The baseline ERP peaks could be captured as described herein with reference to the preceding figures.

The method 1300 includes delivering (1308) a first type of therapy to the user. In some implementations the first type of therapy may include a pharmaceutical treatment, psychological or behavioral therapy, or neuromodulation treatment.

The method 1300 includes—after delivering (1308) the first type of therapy for a period of time—displaying (1311) to the user a second sequence of images. In some implementations, the second sequence of images is delivered in the same manner as the first sequence of images; however, the second sequence of images may include similar but different specific images, and the images may be displayed in a different order. In some implementations, the period of time may be days, weeks or months.

The method 1300 includes capturing (1314) from the user, with the portable EEG headset and in a time-synchronized manner relative to displaying the second sequence of images, a set of intermediate-treatment ERP peaks associated with the second sequence of images. The intermediate-treatment ERP peaks may be captured in the same manner as the baseline ERP peaks.

The method 1300 includes determining (1317) a change of the intermediate-treatment ERP peaks relative to the baseline ERP peaks. In some implementations, determining (1317) a change includes determining that affective measurements (e.g., measurements of pleasantness or intensity) have changed relative to the baseline, possibly signaling progress or change on the part of the user in terms of cue reactivity.

The method 1300 includes delivering (1320) a second type of therapy that is different than the first type of therapy in one situation (e.g., when the determined (1317) change exceeds some threshold (e.g., a percentage change, a percentage decrease or increase in pleasantness or intensity, etc.)), and maintaining delivery of the first therapy in another situation (e.g., when the determined (1317) change is minimal or at least less than a threshold amount). In some implementations, the second type of therapy may include a different type of pharmaceutical therapy, psychological or behavioral therapy, and/or neuromodulation treatment, it may include cessation of pharmaceutical therapy, psychological or behavioral therapy, and/or neuromodulation treatment, and/or it may include providing information (e.g., reports, charts, graphs) to the user (e.g., to reinforce progress made by the user).

While several implementations have been described with reference to exemplary aspects, it will be understood by those skilled in the art that various changes may be made and equivalents may be substituted for elements thereof without departing from the contemplated scope. In some implementations, "approximately" or "substantially" may refer to within about 0.5%, 1%, 2%, 5%, or 10% of a value; in other implementations, these terms ay encompass broader ranges, such as within 20%, 30% or 50% of a value.

Many other variations are possible, and modifications may be made to adapt a particular situation or material to the teachings provided herein without departing from the essential scope thereof. Therefore, it is intended that the scope includes all aspects falling within the scope of the appended claims.

What is claimed is:

1. A system comprising:
   a portable computing device having (a) a graphical user interface for displaying images, (b) a device transceiver, and (c) a computing device processor; and
   a portable electroencephalographic (EEG) headset having (i) a plurality of electrodes configured to capture electrical neural signals of a user wearing the portable EEG headset, (ii) signal processing circuitry configured to create digital information from the captured electrical neural signals; (iii) a headset processor, and (iv) a headset transceiver configured to exchange information with the device transceiver;
   wherein either or both of the computing device processor and the headset processor executes instructions to:
   capture, during a first stage of treatment for substance abuse by the user, during which first stage the user is receiving a first type of therapy, baseline data by displaying a first sequence of images on the graphical user interface; receiving the digital information, simultaneously with and in a time-synchronized manner relative to the displayed first sequence of images; extracting from the digital information, baseline event-related potential (ERP) peaks associated with each image in the first sequence of images, wherein the baseline ERP peaks are time-synchronized to within 1500 ms of the presentation of each corresponding image in the first sequence of images; quantifying affect-related baseline measures associated with the baseline ERP peaks, each baseline affect-related measure comprising a pleasantness aspect and an intensity aspect;
   capture, during a second stage of treatment for substance abuse by the user, comparison data by displaying a second sequence of images on the graphical user interface; receiving the digital information, simultaneously with and in a time-synchronized manner relative to the displayed second sequence of images; extracting from the digital information, comparison ERP peaks associated with each image in the second sequence of images, wherein the comparison ERP peaks are time-synchronized to within 1500 ms of the presentation of each corresponding image in the second sequence of images; quantifying affect-related comparison measures associated with the comparison ERP peaks, each comparison affect-related measure comprising the pleasantness aspect and the intensity aspect;
   compare the quantified comparison affect-related measures to the baseline affect-related measures to determine risk to the user of relapse to substance abuse; and
   based on the determined risk, provide to a clinician involved in treatment for substance abuse of the user, an indication that either the first type of therapy should be maintained or therapy should be transitioned from the first type of therapy to a second type of therapy that is different than the first type of therapy.

2. The system of claim 1, further comprising a centralized computing facility with a data store coupled to the portable computing device by a network, through the device transceiver, the data store stores the baseline data.

3. The system of claim 1, wherein each image in the first sequence of images is temporally separated from a preceding image or a succeeding image by a delay.

4. The system of claim 3, wherein the delay is approximately 250 ms or approximately 500 ms.

5. A system comprising:
   a portable electroencephalographic (EEG) headset, configured to capture EEG signals from a user who is undergoing treatment;
   a computing device having a graphical user interface;
   one or more processors that execute instructions to:
   display a sequence of images on the graphical user interface, each image in the sequence of images having associated therewith an expected affect-related measure of pleasantness and intensity that is expected to evoke an event-related potential (ERP) peak that is greater than a first image-specific threshold and less than a second image-specific threshold;
   receive, from the portable EEG headset, the EEG signals in a manner that is simultaneous to and time-synchronized with the display of each image in the sequence of images;
   extract from the EEG signals, one or more ERP peaks associated with each image, wherein the one more ERP peaks are time-synchronized to within 1500 ms of the display on the graphical user interface of each image in the sequence of images;
   for each image, compare the one or more ERP peaks to the respective first image-specific threshold and to the respective second image-specific threshold;
   based on the comparing for each image, determine a risk to the user; and
   based on the determined risk, provide to a clinician who is treating the user an indication that medication should be added or altered, treatment time should be extended or truncated or type of treatment should be adjusted.

6. The system of claim 5, wherein the risk to the user comprises one of a proclivity to a maladaptive behavior or substance use, or a relapse to use of a substance or engagement of a behavior.

7. The system of claim 5, wherein the first image-specific threshold and the second image-specific threshold are characterized with reference to an electrode on the portable EEG headset.

8. The system of claim 7, wherein the first image-specific threshold and second image-specific threshold are further characterized with reference to a normative population distribution.

9. The system of claim 8, wherein at least one of the first image-specific threshold or the second image-specific threshold corresponds to population-based expected values based on normative ratings of affective pleasantness and intensity of the respective image in the sequence of images.

10. The system of claim 7, wherein the first image-specific threshold and the second image-specific threshold are further characterized with reference to historical data associated with the user.

11. The system of claim 5, wherein extracting the one or more ERP peaks associated with each image comprises identifying a peak or trough within a specified period of time relative to display of the respective image on the graphical user interface.

12. The system of claim 11, wherein the specified period of time is within a range of approximately 150 milliseconds to 1500 milliseconds.

13. A method of treating a user for an addictive or motivational salience disorder, the method comprising:
providing a portable computing device having (a) a graphical user interface for displaying images, (b) a device transceiver, and (c) a computing device processor; and a portable electroencephalographic (EEG) headset having (i) a plurality of electrodes configured to capture electrical neural signals of a user wearing the portable EEG headset, (ii) signal processing circuitry configured to create digital information from the captured electrical neural signals; (iii) a headset processor, and (iv) a headset transceiver configured to exchange information with the device transceiver;
capturing, with the EEG headset and the portable computing device, baseline data by displaying a first sequence of images on the graphical user interface; receiving the digital information simultaneously to and time-synchronized with the displayed first sequence of images; extracting from the digital information, baseline event-related potential (ERP) peaks associated with each image in the first sequence of images, wherein the baseline ERP peaks are time-synchronized to within 1500 ms of the presentation of each corresponding image in the first sequence of images; quantifying affect-related baseline measures associated with the baseline ERP peaks, each baseline affect-related measure comprising a pleasantness aspect and an intensity aspect;
after capturing the baseline data, delivering a first type of therapy to the user during a first stage of treatment, wherein the first stage of treatment comprises days, weeks or months;
after the first stage of treatment, capturing, with the EEG headset and the portable computer device, comparison data by displaying a second sequence of images on the graphical user interface; receiving the digital information simultaneously to and time-synchronized with the displayed second sequence of images; extracting from the digital information, comparison ERP peaks associated with each image in the second sequence of images, wherein the comparison ERP peaks are time-synchronized to within 1500 ms of the presentation of each corresponding image in the second sequence of images; quantifying affect-related comparison measures associated with the comparison ERP peaks, each comparison affect-related measure comprising the pleasantness aspect and the intensity aspect;
comparing the quantified comparison affect-related measures to the baseline affect-related measures to determine a change; and
during a second stage of treatment, when the change is less than a threshold amount, continuing to deliver the first therapy to the user, and when the change is greater than the threshold amount, delivering a second therapy to the user that is different than the first therapy.

14. The method of claim 13, wherein the threshold corresponds to a population-level expected value that is based on a normative rating of affective pleasantness and intensity for a corresponding image.

15. The method of claim 13, wherein the first type of therapy comprises at least one of a pharmaceutical treatment therapy, psychological or behavior modification therapy, or neuromodulation treatment.

16. The method of claim 13, wherein the second type of therapy comprises displaying to the user a report, graph, or chart of historical change in affect-related measures of the user's physiological response to images in the first sequence or the second sequence.

* * * * *